(12) United States Patent
Shimomura et al.

(10) Patent No.: US 7,375,236 B2
(45) Date of Patent: May 20, 2008

(54) METHODS FOR PRODUCING CYCLIC BENZAMIDINE DERIVATIVES

(75) Inventors: Naoyuki Shimomura, Ushiku (JP); Manabu Sasho, Tsukuba (JP); Akio Kayano, Kashima (JP); Kazuhiro Yoshizawa, Kashima-gun (JP); Masahiko Tsujii, Katori-gun (JP); Hiroshi Kuroda, Kashima-gun (JP); Ken Furukawa, Kashima (JP)

(73) Assignee: Eisai Co., Ltd., Tokyo (JP)

( * ) Notice: Subject to any disclaimer, the term of this patent is extended or adjusted under 35 U.S.C. 154(b) by 87 days.

(21) Appl. No.: 11/208,289

(22) Filed: Aug. 18, 2005

(65) Prior Publication Data

US 2006/0058370 A1  Mar. 16, 2006

Related U.S. Application Data

(63) Continuation-in-part of application No. PCT/JP04/001396, filed on Feb. 10, 2004.

(30) Foreign Application Priority Data

Feb. 19, 2003 (JP) ............................. 2003-040949

(51) Int. Cl.
    C07D 265/30    (2006.01)
    C07D 209/44    (2006.01)
    C07C 43/307    (2006.01)

(52) U.S. Cl. .................. 548/471; 544/174; 568/592

(58) Field of Classification Search ................ 548/471; 544/174; 568/592
    See application file for complete search history.

(56) References Cited

U.S. PATENT DOCUMENTS

| | | |
|---|---|---|
| 3,717,648 A | 2/1973 | Diana |
| 3,773,788 A | 11/1973 | Vis |
| 3,859,302 A | 1/1975 | Dixon |
| 3,887,577 A | 6/1975 | Dixon |
| 3,904,395 A | 9/1975 | Eilrich et al. |
| 3,920,688 A | 11/1975 | Eilrich et al. |
| 3,989,709 A | 11/1976 | White et al. |
| 4,004,016 A | 1/1977 | Yale et al. |
| 4,075,342 A | 2/1978 | Sale et al. |
| 4,118,504 A | 10/1978 | Giraldi et al. |
| 4,126,613 A | 11/1978 | Grisar et al. |
| 4,521,793 A | 6/1985 | Kabashima et al. |
| 4,720,581 A | 1/1988 | Mosse et al. |
| 5,143,912 A | 9/1992 | Burner et al. |
| 5,258,387 A | 11/1993 | Burner et al. |
| 5,362,738 A | 11/1994 | Burner et al. |
| 5,677,322 A | 10/1997 | Yasumura et al. |
| 5,935,952 A | 8/1999 | Todo et al. |
| 5,977,134 A | 11/1999 | Ciccarone et al. |
| 6,046,211 A | 4/2000 | Hansen et al. |
| 6,051,718 A | 4/2000 | Freyne et al. |
| 6,077,320 A | 6/2000 | Herve |
| 6,087,380 A | 7/2000 | Hauel |
| 6,114,532 A | 9/2000 | Ries |
| 6,187,799 B1 | 2/2001 | Wood et al. |
| 6,194,447 B1 | 2/2001 | Jensen et al. |
| 6,376,530 B1 | 4/2002 | Claiborne et al. |
| 6,399,837 B1 | 6/2002 | Wilson et al. |
| 7,244,730 B2 | 7/2007 | Suzuki et al. |
| 2004/0004197 A1 | 1/2004 | Sano |
| 2004/0004204 A1 | 1/2004 | Wang |
| 2004/0242627 A1 | 12/2004 | Suzuki et al. |
| 2004/0254376 A1 | 12/2004 | Suzuki et al. |
| 2005/0004197 A1 | 1/2005 | Suzuki et al. |
| 2005/0004204 A1 | 1/2005 | Suzuki et al. |
| 2006/0058370 A1 | 3/2006 | Shimomura et al. |

FOREIGN PATENT DOCUMENTS

DE    2003825 A1   12/1970

(Continued)

OTHER PUBLICATIONS

Nie et al. Medicinal Chemistry Research 1996, 6(5), 318-332.*

(Continued)

*Primary Examiner*—Rebecca Anderson
*Assistant Examiner*—Jason M. Nolan
(74) *Attorney, Agent, or Firm*—Townsend and Townsend and Crew LLP

(57) ABSTRACT

In the present invention, the methods of producing a fluorinated cyclic benzamidine derivative (A), or a salt thereof, comprise the step of reacting a specific novel compound with ammonia or imide.

The methods of this invention for producing a morpholine-substituted phenacyl derivative (B), or a salt thereof, comprise reaction of a specific novel compound with morpholine, reaction of the product with a halogenating reagent, and deketalization of the product.

The methods of this invention for a producing cyclic benzamidine derivative (C), or a salt thereof, comprise the step of coupling compound (A), or a salt thereof, with compound (B), or a salt thereof, in the presence of an ether or a hydrocarbon.

The methods of this invention for recrystallizing a cyclic benzamidine derivative (C), or a salt thereof, comprise the steps of dissolving compound (C), or the salt thereof, in a mixed solvent comprising an alcohol and water, or a mixed solvent comprising an ether and water, and after dissolution, adding additional water to precipitate crystals of compound (C), or the salt thereof.

17 Claims, 1 Drawing Sheet

FOREIGN PATENT DOCUMENTS

| | | |
|---|---|---|
| DE | 2154525 | 6/1972 |
| DE | 2551868 | 8/1976 |
| EP | 364204 | 10/1989 |
| EP | 638075 | 2/1994 |
| EP | 789571 | 5/1996 |
| EP | 842161 | 7/1996 |
| EP | 934280 | 9/1997 |
| EP | 847749 | 6/1998 |
| EP | 1091942 | 7/1999 |
| EP | 1176141 | 3/2000 |
| EP | 1178802 | 11/2000 |
| FR | 8.129 M | 8/1968 |
| GB | 1295478 | 11/1972 |
| GB | 1344663 | 1/1974 |
| JP | 48-42875 | 6/1973 |
| JP | S51-22720 | 2/1976 |
| JP | S51-125071 | 11/1976 |
| JP | 53-71063 | 6/1978 |
| JP | 62-22760 | 1/1987 |
| JP | 4-244083 | 8/1990 |
| JP | 3-50555 | 3/1991 |
| JP | 4-504709 | 8/1992 |
| JP | H07-32103 | 2/1995 |
| JP | H08-225753 | 9/1996 |
| JP | 9-40643 | 2/1997 |
| JP | 10-167965 | 6/1998 |
| JP | 10-509150 | 6/1998 |
| JP | 11-509191 | 8/1999 |
| JP | 2000-503678 | 3/2000 |
| JP | 2002-155060 A | 5/2002 |
| JP | 2003-040949 | 2/2003 |
| WO | WO 83/02920 | 9/1983 |
| WO | WO93/19066 A1 | 9/1993 |
| WO | WO 96/05192 | 2/1996 |
| WO | WO 98/00408 | 1/1998 |
| WO | WO 98/37075 | 8/1998 |
| WO | WO 99/26943 | 6/1999 |
| WO | WO 99/40072 | 8/1999 |
| WO | WO 00/01676 | 1/2000 |
| WO | WO 00/53582 | 9/2000 |
| WO | WO 00/67755 | 11/2000 |
| WO | WO 02/085855 A1 | 10/2002 |
| WO | WO 2004/078721 | 9/2004 |
| WO | WO 06/018954 A1 | 2/2006 |
| WO | WO 06/018955 A1 | 2/2006 |

OTHER PUBLICATIONS

PCT/JP2004/001396, PCT/ISA/237, Apr. 21, 2004.*
WO 2004/078721 A1, Sep. 16, 2004 (PCT/JP2004/001396, PCT/ISA/210, Apr. 20, 2004).*
PCT/JP2004/001396, PCT/ISA/409, Apr. 21, 2004.*
Ahn, et al.,"Structure-Activity Relationships of Pyrroloquinazolines as Thrombin Receptor Antagonists", *Bioorganic & Medicinal Chemistry Letters*, 9: 2073-2078, 1999.
Ahn, et al., "Inhibition of Cellular Action of Thrombin by N3-Cyclopropyl-7-{[4-(1-methylethyl)phenyl]methy}-7H-pyrrolo[3,2-f]quinazoline-1, 3-diamine (SCH 79797), a Nonpeptide Thrombin Receptor Antagonist," *Biochem. Pharm.*, 60: 1425-1434, 2000.
Ahn, Ho-Sam and Samuel Chackalamannil; "Nonpetptide thrombin receptor antagonists;" *Drugs of the Future 2001*; Nov. 2001; pp. 1065-1085; 26:11.
Ahn et al., "Development of Proteinase-Activated Receptor 1 Antagonists as Therapeutic Agents for Thrombosis, Restensosi and Inflammatory Diseases", *Current Pharmaceutical Design*, 2349-65, 2003.
Alfaia, et al., "Quaternization Reaction of Heterocyclic Imines in Methanol - A Case of Strong Anti-Reactivity Selectivity Principle with Isoselective Temperature", *European Journal of Organic Chemistry*, 3627-3631, 2000.

Aly, Ashraf A., et al.; Chemical Abstracts; "Reactions of phenylisoindoles with some selected organic acceptors;" *Heterocycl. Commun.*; 1997; p. 698; 127: 81319b.
Andrade-Gordon, et al., "Design, Synthesis, and Biological Characteriastion of a Peptide-mimetic Antagonist for a Tethered-ligand Receptor," *PNAS*, 96: 12257-12262, 1999.
Anisimova, et al., "Imidazo [1, 2-a] Benzimidazole Derivatives. X. Nitration of 2, 9-Disubstituted Imidazo [1, 2-a] Benzimidazole," *Khim. Geterotsikl. Soedin*, 2: 258-262, 1975.
Anisimova, et al., "Imidazo [1, 2-a] Benzimidazole Derivatives. 22. Synthesis of 2, 3-dihydroimidazo [1, 2-a]benzimidazoles from 3-(2-hydroxyethyl)-2-iminobenzimidazolines," *Khim. Geterotsikl. Soedin*, 7: 918-925, 1986.
Anisimova, et al., "Imidazo [1, 2-a] Benzimidazole Derivatives. 25. Reaction of 2, 9-disubstituted Imidazo [1, 2-a]benzimidazoles With Acrylic Acids and Their Derivatives," *Khim. Geterotsikl. Soedin*, 11: 1496-1502, 1987.
Anismova, V. A., et al.; "Synthesis and pharmacological activity of certain 2,3-dihydroimadazo[1, 2-a]benzimidazoles and intermediates formed in their synthesis;" *Khimiko-Farmatseviticheskii Zhurnal*; 1987; pp. 313-319; 21:3.
Babichev, F. S., et al.; "Derivatives of s-Triazolo[5, 1-a]Isoindole;" *Ukr. Khim. Zh.*; 1981; pp. 291-295; 47:3.
Babichev, F. S., et al.: "Reaction of o-Chloromethylbenzonitrile with Acid Hydrazides;" *Ukr. Khim. Zh.*; 1981; pp. 735-738; 47:7.
Babichev,et al, "The Structure of Products of the Reaction of 1-Amino-3H-Isoindole with Benzyle Chloride and α-Bromoketones," *Ukr. Khim. Zh.*, 50: 623-626, 1984 (original and abstract).
Babichev, F. S., et al.; "Reactions of o-(chloromethyl)benzonitrile with amines. Condensation of p-(chloromethyl)benzonitrile with aromatic and aliphatic amines;" *Chemical Abstracts*; 1970; p. 335; 72:132428s.
Babichev, F. S., et al.; "Condensation of o-(chloromethyl)benzonitrile with phenylenediamines;" *Chemical Abstracts*; 1972; p. 442; 76:153482c.
Babichev, F. S., et al.; "1-Imino-2-Alkylacylisoidolines;" *Ukr. Khim. Zh.*; 1984; pp. 1105-1110; 50:10.
Babichev, F. S., et al.; "5H-s-Triazolo[5, 1-a]isoindole;" *Chemical Abstracts*; 1985; p. 587; 102:220805f.
Babichiev, et al., "Structure of the Salts of 2-amino. DELTA. 1-pyrroline with Benzyl Chloride and alpha-halo Ketones," *Ukr. Khim. Zh.*, 52:398-401, 1986.
Bernatowicz, et al. "Development of Potent Thrombin Receptor Antagonist Peptides", *J. Med. Chem.* 39: 4879-4887, 1996.
Caroti, et al., "A Facile Synthesis of 5,7-Dihydro-5-Oxopyrido [3',2':5,6] Pyrimido-[1,2-a] Benzimidazoles. A New Heterocyclic Ring System", *J. Heterocycl. Chem.*, 23(6): 1833-1836; 1986.
Chackalamannil, S., et al.; "Discovery of potent, nonpeptide thrombin receptor antagonists (oral presentation);" *Proceedings of the 221st ACS National Meeting*; Apr. 1-5, 2001; p. 342.
Chackalamannil, et al., "Potent, Low Molecular Weight Thrombin Receptor Antagonists," *Bioorg. Med. Chem. Lett.*, 11: 2851-2853, 2001.
Clemens, Andrea, et al.; "3-Hydroximino-1-alkyl(aryl)-isoindolines and 3-Hydroxylamino-1-alkyl(aryl)-1H-isoindiles-Model Compounds for Investigations of Structure and Reactivity;" *Z. Naturforsch*; Aug. 6, 1996; pp. 1791-1810; 51:12.
Cohen, et al., "Enantiospecific Synthesis of Leukotrienes $C_4$, $D_4$, and $E_4$ and [14, 15-$^3$H2] Leukotriene $E_4$ Dimethyl Ester", *J. Am. Chem. Soc.* 105: 3661-3672, 1983.
Compernolle, et al., "Synthesis and Preliminary in vitro Metabolic Studies on N,N-Dimethyl-N'-2-Imidazolyl-N'-Benzyl-1,2-Ethanediamine, an Analog of the Carcinogenic Antihistamine Methapyrilene", *J. Heterocyclic Chem.*, 19:1403-1408, 1982.
Supplementary Partial European Search Report in a corresponding EP application No.: EP 02720534.
Cunningham et al., "Protease-activated receptor 1 mediates Thrombin-dependent, cell-mediated renal inflammation in crescentic glomerulonephritis", *J. Exp. Med.*, 2000 191(3): 455-61.
Da Settimo, et al., "Synthesis of 2-Methlaminobenzimidazole Derivatives Tested for Antiinflammatory Activity", *Farmaco*, 49(12): 829-834, 1994.

Da Settimo, et al., "Synthesis and Anti-Inflammatory Properties of 2-Amino-Benzimidazole Derivatives", *Farmaco*, 47(10): 1293-1313, 1992.

Da Settimo, et al., "Synthesis and Antihypertensive Activity of Some 2-Aminobenzimidazole and Indole Derivatives", *Farmaco*, 46(2): 357-367, 1991.

Da Settimo, et al., "Synthesis and Evaluation of Aminoadamantane Derivatives for In Vitro Anti-HIV and Antitumor Activities", *Farmaco*, 50(5): 321-326, 1995.

Dixon, et al., "Bioactive Diversity and Screening Library Selection via Affinity Fingerprinting", *J.Chemical Information and Computer Sciences*, 38(6): 1192-1203, 1998.

Eynde, J. J. Vanden, et al.; "Novel Syntheses of Heterocycles with N-(1-Haloalkyl)Azinium Halides. Part 3, Preparation of 2-Aryl-1-Arylimino-2, 3-Dihydro-1H-Isoindoles;" *Bulletin Soc. Chim. Belg.*; 1992; pp. 509-512; 101:6.

Even-Ram, et al., "Thrombin receptor overexpression in malignant and physiological invasion processes", *Nature Medicine*, 1998, 4(8):909-14.

Gabazza et al., "Thrombin in the airways of asthmatic patients", *Lung*, 1999, 177(4):253-62 (Abstract only).

Görlitzer, Klaus; "Zur Cyclisierung von Phthalaldehyd mit Acetophenonen;" *Arch. Pharm.*; 1976; pp. 356-366; 309:5.

Görlitzer, Klaus and Dietrich Buss; "Zur Reaktion von Phthalaldehyd mit Anthransilsäureestern;" *Arch Pharm.*; 1985; pp. 735-743; 318.

Hauck et al., "α-Thrombin stimulates contraction of human bronchial rings by activation of protease-activated receptors", *Am. J. Physiol.*, 1999, 277:L22-L29.

Hinton, I. G., et al.; "Cyclic oxo-amines IV. Synthesis and reactions of 1,2,3,4-tetrahydro-2methyl-4oxoisoquinoline;" Chemical Abstracts; 1959; 53:15082h-15085d.

Hinton, I. G., et al.; "Interaction of o-chloromethylphenacyl chloride and primary amines: a novel formation of the isoindoline system;" *Chemical Abstracts*; 1959; 53:16106c-16107d.

Hoekstra, "Thrombin Receptor (PAR-1) Antagonists. Heterocycle-Based Peptidomimetics of the SFLLR Agonist Motif", *Bioorganic & Medicinal Chemistry Letters*, 8: 1649-1654, 1998.

Hung, et al., "Thrombin-Induced Events in Non-Platelet Cells are Mediated by the Unique Proteolytic Mechanisms Established for the Cloned Platelet Thrombin Receptor", *The Journal of Cell Biology*, 116(3): 827-832, 1992.

Hung, et al., " Cloned Platelet Thrombin Receptor is Necessary for Thrombin-Induced Platelet Activation", *J. Clin. Invest.*, 89: 1350-1353, 1992.

Janusz, et al., "New Cyclooxygenase-2/5-Lipoxygenase Inhibitors. 1. 7-tert-Butyl1-2,3-Dihydro-3,3-Dimethylbenzofuran Derivatives as Gastrointestinal Safe Antiinflammatory and Analgesic Agents: Discovery and Variation of the 5-Keto Substituent", *J. Med. Chem.* 41: 1112-1123, 1998.

Junge et al., "The contribution of protease-activated receptor 1 to neuronal damage caused by transient focal cerebral ischemia", *PNAS*, 2003, 100(22):13019-024.

Kato, et al., "In Vitro Antiplatelet Profile of FR171113, a Novel Non-peptide Thrombin Receptor Antagonist," *Europ. J. Pharm.*, 384:197-202, 1999.

Kawahara, T., et al.; "Discovery and Optimization of Potent Orally Active Small Molecular Thrombin Receptor(PAR-1) Antagonists;" *Proceedings from the Fifth AFMC International Medicinal Chemistry Symposium*; Oct. 14-17, 2003; p. 137; A-100.

Kawahara, Tetsuya, et al.; "Discovery and Optimization of Potent Orally Active and Small Molecular Thrombin Receptor(PAR-1) Antagonists;" *Proceedings from the 227th ACS National Meeting*; Mar. 28-Apr. 1, 2004; MEDI 85.

Kigasawa, Kazuo, et al.; "Synthesis of Optically Active 2-[4-(1-Oxo-2-isoindolinyl)phenyl]propanoic Acid;" *Journal of Heterocyclic Chemistry*; May 1978; pp. 369-375; 15:3.

Klötzer et al., "Acylderivate von 2-Amino-1-pyrrolinen", *Monatshefte Fur Chemie*, 102(2): 627-634, 1971.

Korbonits, et al., "4-Aminobutanoic Amidoxime Derivatives. Synthesis of 1-Substituted 2-Hydroximinopyrrolidines, a Novel Type of Lactames," *Acta. Chim. Hung.*, 117: 239-245, 1984.

Koshchienko, et al., "Synthesis and Antibacterial Activity of 3-(alkoxymethyl)-2-amino-1-methylbenzimidazolium Chlorides," *Khim. Farm. Zh.*, 11: 14-17, 1977.

Koshchienko, et al., "New Synthesis of Imidazo [1, 2-a] Benzimidazole Derivatives," *Khim. Geterotsikl. Soedin.*, 1: 140-141, 1975.

Kovalev, et al., "Synthesis and Pharmacological Properties of Some Disubstituted Imidazo[1, 2-a] Benzimidazole Derivatives," *Khim. Farm. Zh.*, 13: 57-62, 1979.

Kovtunanko, V. A., et al.; *Vest.Kiev.Un-ta.Khimiya*; 1985; pp. 21-25; 26.

Kovtunenko, V. A., et al., "Preparation and Reactions of 1R-2-iminopyrrolidines," *Ukr. Khim. Zh.*, 52: 63-70, 1986.

Kovtunenko, V.A., et al., "6,7-Dihydro-5H-pyrrolo[1,2-a]imidazole Derivatives," *Ukr. Khim. Zh.*, 52: 647-651, 1986.

Kovtushenko, V. A., et al; "1-Amino-2R-3H-Isoindolium Salts;" *Ukr. Khim. Zh.*; 1984; pp. 530-534; 50:5.

Kovtushenko, V. A., et al; "1-Imino-2R-and 1-Imino-2R-3Phenylisoidolines," *Ukr. Khim. Zh.*; 1984; pp. 1198-1203; 50:11.

Kovtushenko, V. A., et al; "Derivatives of 5H-Imidazo[2,1-a]Isoindole;" *Ukr. Khim. Zh.*; 1985; pp. 644-649; 51:6.

Kovtushenko, V. A., et al; "Synthesis of Pyrido[1,2-b][2,4]Benzodiazepine-6(11H)-Imines;" *Khimiya Geterotsiklicheskikh Soedinenii*; 1987; pp. 1264-1269; 9.

Kreher, Richard and Hans Hennige; "Reaktionen von 1-Alkoxy-isoindolenin (Reactions of 1-Alkoxy-isoindolinenes);" *Z. Naturforsch*; 1973; pp. 801-804; 28:11-12.

Kuz'menk, et al., "Synthesis of 9-aminoimidazo [1, 2-a]benzimidazoles and Their Deamination," *Khim. Geterotsikl. Soedin*, 11:1517-1523, 1990.

Langlois, et al., "Synthesis of New Bicyclic Amidines. 1. Derivatives of Imidazole, 1,3,4-Triazole and Tetrazole," *J. Heterocycl. Chem*, 19: 193-200, 1982.

Latli, et al., "Novel and Potent 6-Chloro-3-pyridinyl Ligands for the α4β2 Neuronal Nicotinic Acetylcholine Receptor," *J. Med. Chem.*, 42: 2227-2234, 1999.

Lessel, J., "Benzodiazepine Und Isoindole Durch Acylierung Von Amidinen Benzodiazepines And Isoindoles By Acylation Of Amidines," *Pharmazie*, 48(11): 812-816, 1993.

Lipinski, et al., "Bioisosteric Prototype Design of Biaryl Imidazolyl and Triazolyl Competitive Histamine $H_2$ - Receptor Antagonists", *J. Med. Chem.* 29: 2154-2163, 1986.

Liu, et al., "The Mechanisms of Titanium Complex-Catalyzed Reduction of Aryl Halides by Sodium Borohydride is Strongly Solvent Dependent", *J. Org. Chem.* 59: 940-942, 1994.

Mancuso and Swern, "Activated Dimethyl Sulfoxide: Useful Reagents for Synthesis", *Reviews*, 165-185, 1981.

Marty et al., "Amelioration of collagen-induced arthritis by thrombin inhibition", *J. Clin. Invest.*, 2001, 107(5):631-40.

May, et al. "Chemie Und Biologische Eigenschaften Substituierter 3-Amino-1H-Isoindole," *Arzneim.-Forsch*, 30(11): 1487-1493, 1980.

McComsey , et al., "Macrocyclic Hexapeptide Analogues of the Thrombin Receptor (PAR-1) Activation Motif Sfllrn" *Bioorganic & Medicinal Chemistry Letters*, 9: 255-260, 1999.

Nannini, G., et al.; "New Analgesic-Anti-inflammatory Drugs;" *Arzneim-Forsch*; 1973; pp. 1090-1100; 23:8.

Nantermet, et al., "Nonpeptidic small-molecule antagonists of the human platelet thrombin receptor (PAR-1)", *221st ACS National Meeting (San Diego)/ MEDI/Protease-Activated Receptor Antagonists*, Paper 341: (Oral), Wed Apr. 4, 2001. (Abstract only).

Ngaiza, et al., "A 14 Amino Acid Peptide Derived from the Amino Terminus of the Cleaved Thrombin Receptor Elevates Intracellular Calcium and Stimulates Prostacyclin Production in Human Endothelial Cells", *Biochem. & Biophys. Res. Comm.*, 179(3): 1656-1661, 1991.

North, et al., "A Study of Some I-Alkyl-2,3-Dihydroimidazo [1,2-a] Benzimidazoles", *Journal of Heterocyclic Chemistry*, 6(5): 655-662, 1969.

Ogura, et al., "Studies on Heterocyclic Compounds, 10. Synthesis of Some Imidazo [1,2-α] Benzimidazoles with Potent Analgetic Activities", Journal of Medicinal Chemistry, 15(9): 923-926, 1972.

O'Sullivan, R.D. and Parkins, A.W., "The Synthesis Of N-Heterocycles Using Ortho-Metallated Primary Benzylamine Complexes Of Palladium And Platinum," *J. Chem. Soc., Chem. Commun.*, 17: 1165-1166, 1984.

"Oxazines And Thiazines," *Chemical Abstracts*, 78: 478, 1973. (Abstract No. 111227).

Poos, George I.; "Pharmacologically active 1-alkyl-2-(aralkylimino) pyrrolidines;" *Chemical Abstracts*; 1972; 77:419523.

Rehse, et al., "New NO-Donors with Antithrombotic and Vasodilating Activities", XI. 2-Nitrosiminobenzimidazoles, *Arch. Pharm.* 328:(1) 77-80, 1995.

Sarembock, et al., "Effectiveness of Recombinant Desulphatohirudin in Reducing Restenosis After Ballon Angioplasty of Atherosclerotic Femoral Arteries in Rabbits", *Circulation*, 84: 232-243, 1991.

Sato, et al., "Organic Solvent - and Halide Free Oxidation of Alcohols with Aqueous Hydrogen Peroxide", *J. Am. Chem. Soc.* 119: 12386-12387, 1997.

Sawanish, H. and Tsuchiya, T., "Synthesis And Characterization Of 1H-2, 4-Benzodiazepines," *Heterocycles*, 22(12): 2725-2728, 1984.

Sawanishi, H., et al., "Studies On Diazepines. XXI. Photochemical Synthesis Of 1H-2, 4-Benzodiazepines From 4-Azidoisoquinolines," *Chem. Pharm. Bull.*, 33(10): 4564-4571, 1985.

Study Report, Eisai Co., Ltd., "E5555: Protease-activated Receptor-1 Binding of E5555 in Human Platelet Membrane", Tsukuba Research Laboratories, Japan: Study No. MO1035 (2002).

Study Report, Eisai Co., Ltd., "E5555: Inhibitory Effect of E5555 on Human Platelet Aggregation in vitro", Tsukuba Research Laboratories, Japan: Study No. M0 1027 (2002).

Study Report, Eisai Co., Ltd., "E5555: Inhibitory Effect of Rat Smooth Muscle Cell Proliferation", Tsukuba Research Laboratories, Japan; Study No. M01038 (2002).

Tawada, et al., "Studies on Antidiabetic Agents. IX. A New Aldose Reductase Inhibitor, AD-5467, and Related 1,4-Benzoxazine and 1,4-Benzothiazine Derivatives: Synthesis and Biological Activity", *Chem. Pharm. Bull.* 38(5): 1238-1245, 1990.

Toja, E., et al., "Synthesis And Pregnancy Terminating Activity Of 2-Arylimidazo '2, 1-a! Isoquinolines And Isoindoles," *Arzneim.-Forsch*, 33(11):1222-6, 1983.

Tytlin, A. K., et al.; "Synthesis and reactions of isoindole[2, 1-a][2-4]=benzodiazepine;" *Chemical Abstracts*; 1985; p. 620; 103: 104932s.

Vassallo, et al. "Structure-Function Relationships in the Activation of Platelet Thrombin Receptors by Receptor-Derived Peptides", *J. Bio. Chem.*, 267(9): 6081-6085, 1992.

Vergnolle et al., A role for proteinase-activated receptor-1 in inflammatory bowel disease:, *J. Clin. Invest.*, 2004, 114(10):1444-56.

Vu, et al., "Molecular Cloning of a Functional Thrombin Receptor Reveals a Novel Proteolytic Mechanism of Receptor Activation", *Cell*, 64: 1057-1068, 1991.

Vu. et al., "Domains Specifying Thrombin-Receptor Interaction", *Nature*, 353: 674-677, 1991.

Yale and Bristol, "1-Aralkyl-2(1H)-Pyridinimines and Their Derivatives," *J. Heterocycl. Chem*, 12: 1027-1029, 1975.

Yale, et al., "Quaternary Derivatives for 2-Aminobenzimidazole and 2-Phenylethyl-and Phenyloxymethyl Halides", *I.J. Heterocycl, Chem.*, 15(3): 505-507, 1978.

Yang et al., "Reduction of arthritis severity in protease-activated receptor-deficient mice", *Arthritis & Rheumatism*, 2005, 52(4):1325-32.

Yoshikawa, Seiji; "Methods For Producing Dibromofluorobenzene Derivatives;" U.S. Appl. No. 11/573,882; Filed Aug. 3, 2007; Not Yet Published; Stored in the USPTO's IFW system.

Yoshikawa, Kazuhiro, et al.; "Methods For Producing Isoindole Derivatives;" U.S. Appl. No. 11/573,814; Int'l. Filing Date Jul. 27, 2005; Not Yet Published; Stored in the USPTO's IFW system.

Zhao, et al., "A Novel Chromium Trioxide Catalyzed Oxidation of Primary Alcohols to the Carboxylic Acids", *Tetrahedron Letters*, 39: 5323-5326, 1998.

* cited by examiner

METHODS FOR PRODUCING CYCLIC BENZAMIDINE DERIVATIVES

This application is a continuation-in-part of PCT/JP04/001396, filed Feb. 10, 2004, which claims priority from Japanese Patent Application No. 2003-040949, filed Feb. 19, 2003. The entirety of all of the aforementioned applications are incorporated herein by reference.

TECHNICAL FIELD

The present invention relates to methods for producing cyclic benzamidine derivatives, recrystallization methods thereof, their intermediates, and methods for producing the intermediates.

BACKGROUND ART

One of the approaches against thrombosis is the inhibition of the enzyme activity towards thrombin. Recently, compounds having antagonistic effects on thrombin receptors are expected to exhibit excellent effects for the treatment and prevention of thrombin-related diseases such as thrombosis, vascular restenosis, deep phlebothrombosis, pulmonary embolism, cerebral infarction, cardiac diseases, disseminated intravascular coagulation syndrome, hypertension, inflammatory diseases, rheumatism, asthma, glomerulonephritis, osteoporosis, nerve disorders, malignant tumors, and so on. Accordingly, there was a need for thrombin receptor antagonists that satisfy points such as pharmacological activity, receptor specificity to thrombin receptors, safety, dose and oral usefulness.

The present inventors have already found that 2-iminopyrrolidine derivatives and their salts have excellent thrombin receptor-inhibitory activity, and are useful as thrombin receptor antagonists (Patent Document 1: WO02/085855). Among the 2-iminopyrrolidine derivatives and their salts disclosed in Patent Document 1, methods for producing 1-(3-tert-butyl-4-methoxy-5-morpholino-phenyl)-2-(5,6-diethoxy-7-fluoro-1-imino-1,3-dihydro-2-isoindol-2-yl)-ethanone (hereinafter may be referred to as "cyclic benzamidine derivative (C)") represented by formula (XIII),

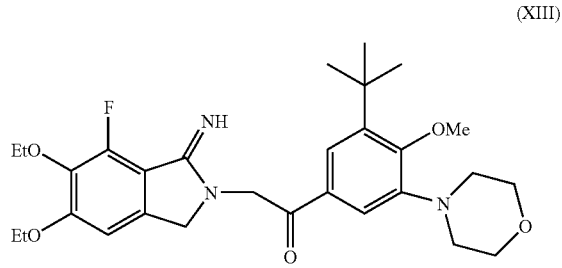

(XIII)

or a salt thereof, are described in Patent Document 1.

More specifically, as an example of methods for producing the cyclic benzamidine derivative (C) in the presence of N,N-dimethylformamide (DMF) as a solvent, Patent Document 1 discloses the method of coupling 5,6-diethoxy-7-fluoro-3H-isoindol-1-ylamine represented by the following formula:

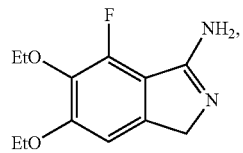

or 5,6-diethoxy-7-fluoro-1,2-dihydroisoindol-1-ylimine represented by

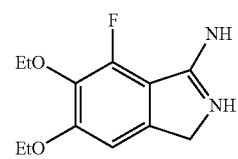

(hereinafter, these compounds may be referred to as "fluorinated cyclic benzamidine derivative (A)"), and 2-bromo-1-(3-tert-butyl-4-methoxy-5-morpholinophenyl)ethanone represented by the following formula:

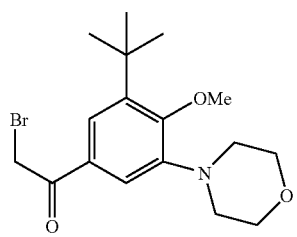

(hereinafter, it may be referred to as "morpholine-substituted phenacyl derivative (B)").

A method of producing the fluorinated cyclic benzamidine derivative (A) is described as dissolving 4,5-diethoxy-3-fluorophthalonitrile, which is represented by the following formula, in ethylacetate-ethanol-methanol, and adding platinum oxide.

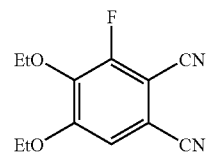

However, this method has a low yield of the desired compound, leads to formation of numerous by-products, and requires purification immediately after the reaction due to product instability. Furthermore, since the products have high adsorptivity for the platinum catalyst, treatments to avoid hazardous ignition from the remaining platinum catalyst are necessary even after catalyst filtration, thus posing complicated purification issues. Patent Document 1 uses a known compound 1,2-diethoxy-3-fluorobenzene as the raw material for producing a fluorinated cyclic benzamidine derivative (A), but its low overall yield was a problem.

Therefore, methods of producing the fluorinated cyclic benzamidine derivative (A), or a salt thereof, that give high overall yields, have easy reaction procedures, and are useful even in an industrial scale production were anticipated.

Patent Document 1 discloses a method of producing the morpholine-substituted phenacyl derivative (B) using 2-tert-butylphenyl as the raw material. However, this method has problems such as: the necessity to include manipulations to secure safety since a nitro compound is used in the reaction procedure; the need to use expensive reagents such as 2-bromoethylether; and low overall yield.

Therefore, economical and industrially advantageous methods for producing the morpholine-substituted phenacyl derivative (B) or a salt thereof, which have simple reaction procedures and give high overall yields were required.

Furthermore, the reaction of coupling the fluorinated cyclic benzamidine derivative (A) or a salt thereof with the morpholine-substituted phenacyl derivative (B) to obtain the cyclic benzamidine derivative (C) or a salt thereof also had complicated purification procedure issues.

Therefore, there was a need for overall industrially advantageous methods for producing the cyclic benzamidine derivative (C), or a salt thereof, including methods of synthesizing raw materials such as the aforementioned compound (A) and compound (B).

DISCLOSURE OF THE INVENTION

More specifically, an ultimate objective of the present invention is to provide effective methods for producing the cyclic benzamidine derivative (C) or a salt thereof. Therefore, the initial objective is to provide effective methods for producing raw materials for synthesizing the cyclic benzamidine derivative (C), which are the fluorinated cyclic benzamidine derivative (A) or a salt thereof, and the morpholine-substituted phenacyl derivative (B) or a salt thereof, as well as to provide their precursors. Another objective is to provide effective methods for coupling the fluorinated cyclic benzamidine derivative (A) or a salt thereof with the morpholine-substituted phenacyl derivative (B) or a salt thereof, as well as effective methods for recrystallizing the cyclic benzamidine derivative (C) or a salt thereof.

Upon extensive studies to solve the above-mentioned issues, the present inventors succeeded in synthesizing the fluorinated cyclic benzamidine derivative (A) or a salt thereof with simple and convenient procedures and good yields, using the novel compound (I) represented by formula (I)

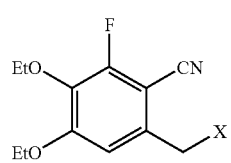

(I)

(wherein X represents a leaving group), as the raw material for synthesis.

Furthermore, by using a novel compound represented by formula (IX)

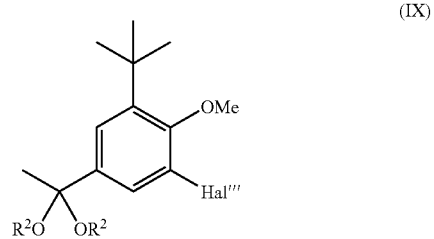

(IX)

(wherein, each of the two $R^2$s represents an alkyl group of 1 to 4 carbons, and the two $R^2$s can be bonded to each other and form a cyclic group represented by —$(CH_2)_n$— (wherein n represents an integer of 2 to 4); Hal''' represents a halogen atom) as the raw material for synthesis, the inventors successfully synthesized the morpholine-substituted phenacyl derivative (B) or a salt thereof by simple and convenient procedures.

Furthermore, the present inventors discovered that when an ether, (preferably tetrahydrofuran (THF)), or a hydrocarbon, is used as the reaction solvent in the coupling reaction between the fluorinated cyclic benzamidine derivative (A) or a salt thereof and the morpholine-substituted phenacyl derivative (B) or a salt thereof, the desired cyclic benzamidine derivative (C) or a salt thereof can be crystallized easily and desired compounds can be readily and conveniently purified.

In addition, the present inventors found that cyclic benzamidine derivative (C) can be dissolved readily at a low temperature and recrystallized easily by dissolving this cyclic benzamidine derivative (C) in a mixed solvent prepared from an alcohol and water, or an ether and water, and precipitating its crystals by adding water, and thereby completed this invention.

More specifically, the present invention relates to the following:

[1] a method for producing a fluorinated cyclic benzamidine derivative (A) represented by formula (II) (wherein Et represents an ethyl group), or a salt thereof,

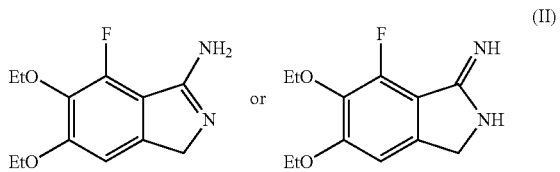

(II)

wherein the method comprises the step of reacting a compound represented by formula (I)

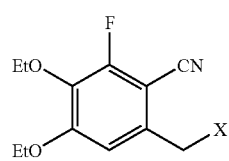

(I)

(wherein, X represents a leaving group) with ammonia or an imide;

[2] the method of [1], comprising the step of reacting the compound represented by formula (I) in which X is —OSO$_2$R$^1$ (wherein, R$^1$ represents a C$_{1-6}$ alkyl group, a halogenated C$_{1-6}$ alkyl group, a C$_{6-10}$ aryl group, or a halogenated C$_{6-10}$ aryl group) with ammonia;

[3] the method of [1], comprising the steps of:

(a) reacting the compound represented by formula (I) in which X is —OSO$_2$R$^1$ (wherein, R$^1$ represents a C$_{1-6}$ alkyl group, a halogenated C$_{1-6}$ alkyl group, a C$_{6-10}$ aryl group, or a halogenated C$_{6-10}$ aryl group), with a phthalimide or a succinimide, or a metal salt thereof, and (b) converting the compound obtained in step (a) into an amine derivative;

[4] the method of [1], comprising the step of reacting the compound represented by formula (I) in which X represents a halogen atom, with ammonia;

[5] the method of [1], comprising the steps of:

(a) reacting the compound represented by formula (I) in which X represents a halogen atom, with a phthalimide or a succinimide, or a metal salt thereof, and (b) converting the compound obtained in step (a) into an amine derivative;

[6] the method of [2] or [3], wherein a compound represented by formula (I')

(wherein, R$^1$ represents a C$_{1-6}$ alkyl group, a halogenated C$_{1-6}$ alkyl group, a C$_{6-10}$ aryl group, or a halogenated C$_{6-10}$ aryl group) is obtained by reacting a compound represented by formula (III)

(wherein, Et represents an ethyl group), with R$^1$SO$_2$Y or (R$^1$SO$_2$)$_2$O (wherein, R$^1$ represents a C$_{1-6}$ alkyl group, a halogenated C$_{1-6}$ alkyl group, a C$_{6-10}$ aryl group, or a halogenated C$_{6-10}$ aryl group, and Y represents a halogen atom);

[7] the method of [4] or [5], wherein the compound represented by formula (I")

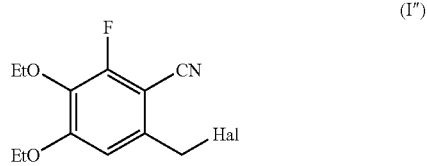

(I")

(wherein, Hal represents a halogen atom) is obtained by reacting a compound represented by formula (III)

(wherein, Et represents an ethyl group) with a halogenating reagent;

[8] the method of [4] or [5], wherein the compound represented by formula (I")

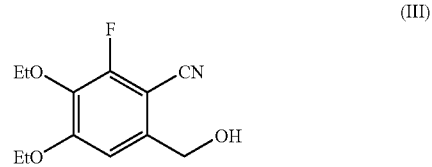

(I")

(wherein, Hal represents a halogen atom), is obtained by reacting a compound represented by formula (IV)

(wherein, Et represents an ethyl group), with a halogenating reagent;

[9] the method of [6] or [7], wherein the compound represented by formula (III) is obtained by steps comprising the following (1) to (3):

(1) reacting a compound represented by formula (V)

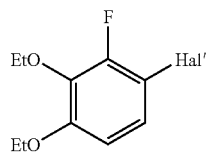
(V)

(wherein, Hal' represents a halogen atom) with a cyanation reagent to obtain a compound represented by formula (VI)

(VI)

(2) obtaining a compound represented by formula (VII)

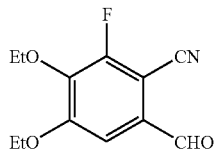
(VII)

through a formylation reaction of the compound represented by formula (VI); and (3) obtaining the compound represented by formula (III)

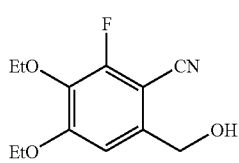
(III)

(wherein, Et represents an ethyl group) by reducing the compound represented by formula (VII);

[10] the method of [4] or [5], wherein the compound represented by formula (I")

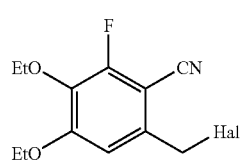
(I")

(wherein, Hal represents a halogen atom) is obtained by steps comprising the following (1') to (3') described below:

(1') reacting a compound represented by formula (V)

(V)

(wherein, Hal' represents a halogen atom) with a cyanation reagent to obtain a compound represented by formula (VI)

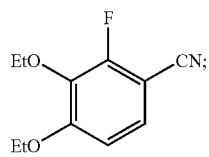
(VI)

(2') obtaining the compound represented by formula (IV)

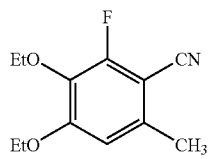
(IV)

through a methylation reaction of the compound represented by formula (VI); and (3') obtaining the compound represented by formula (I") (wherein Et represents an ethyl group) by reacting the compound represented by formula (IV) with a halogenating reagent;

[11] a method for producing a morpholine-substituted phenacyl derivative (B) represented by formula (VIII)

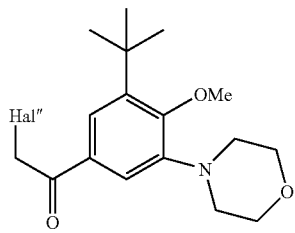
(VIII)

(wherein, Hal" represents a halogen atom) or a salt thereof, wherein the method comprises the following steps of (1") to (3"):

(1") reacting a compound represented by formula (IX)

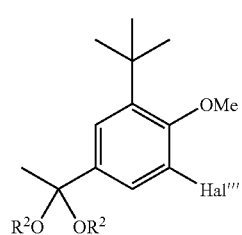
(IX)

(wherein, each of the two R²s represents a C₁₋₄ alkyl group, and the two R²s may be bonded to each other to form a cyclic group represented by —(CH₂)ₙ— (wherein, n represents an integer of 2 to 4); Hal'" represents a halogen atom) with morpholine to obtain a compound represented by formula (X)

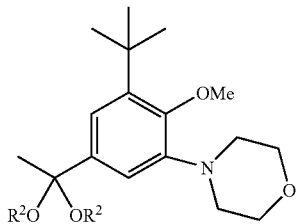
(X)

(wherein, R² represents the same group as in formula (IX));

(2") reacting a compound represented by formula (X) with a halogenating reagent to obtain a compound represented by formula (XI)

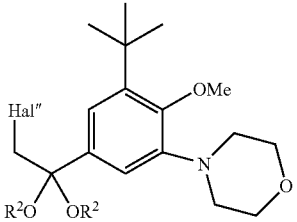
(XI)

(wherein, R² represents the same group as in formula (IX), and Hal" represents a halogen atom);

(3") performing a deketalization reaction on a compound represented by formula (XI) to obtain a morpholine-substituted phenacyl derivative (B) represented by formula (VIII)

(In the above formulas, Me represents a methyl group);

[12] the method of [11], wherein the compound represented by formula (IX)

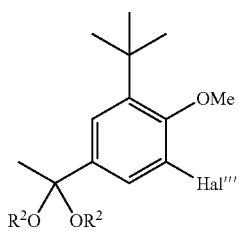
(IX)

(wherein, each of the two R²s represents a C₁₋₄ alkyl group, and the two R²s may be bonded to each other to form a cyclic group represented by —(CH₂)ₙ— (wherein, n represents an integer of 2 to 4, and Me represents a methyl group); Hal'" represents a halogen atom) is obtained through the steps of: ketalization of a compound represented by formula (XII)

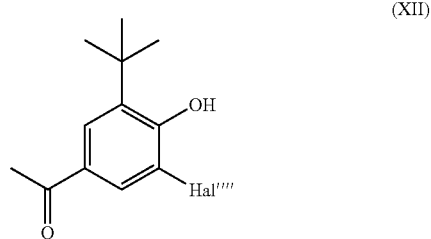
(XII)

(wherein, Hal"" represents a halogen atom), by reacting with R²OH, HC(OR²)₃ (wherein R² represents a C₁₋₄ alkyl group), or HO—(CH₂)ₙ—OH (wherein, n represents an integer of 2 to 4); and methoxylation of the hydroxyl group in the compound represented by formula (XII);

[13] a method for producing a cyclic benzamidine derivative (C), wherein the method comprises reacting a fluorinated cyclic benzamidine derivative (A) represented by formula (II),

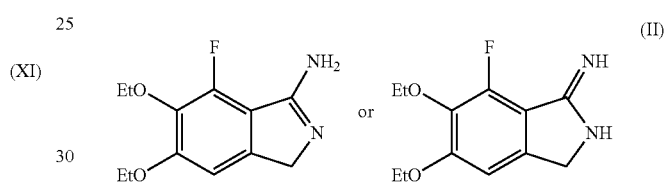
(II)

or a salt thereof, with a morpholine-substituted phenacyl derivative (B) represented by formula (VIII)

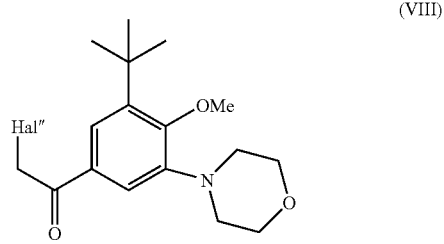
(VIII)

(wherein, Hal" represents a halogen atom), or a salt thereof, in the presence of at least one type of solvent selected from a group consisting of ethers and hydrocarbons to obtain a compound represented by formula (XIII)

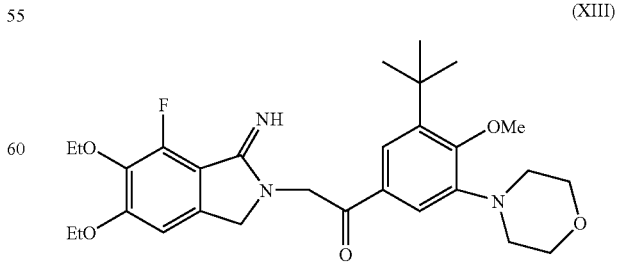
(XIII)

or a salt thereof (In the above formulas, Me represents a methyl group, and Et represents an ethyl group);

[14] the method of [13], wherein the solvent is an ether;

[15] the method of [14], wherein the ether is tetrahydrofuran;

[16] a method for producing a cyclic benzamidine derivative (C), wherein the method comprises the steps of reacting a fluorinated cyclic benzamidine derivative (A) represented by formula (II)

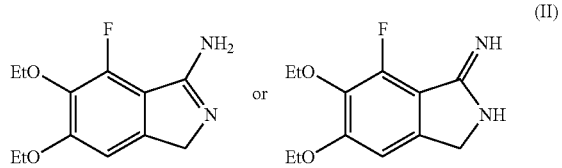

or a salt thereof, with a morpholine-substituted phenacyl derivative (B) represented by formula (VIII)

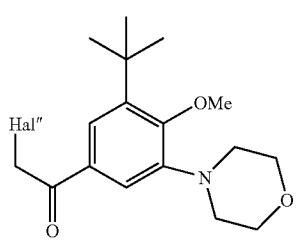

(wherein, Hal" represents a halogen atom), or a salt thereof, to generate a compound represented by formula (XIII)

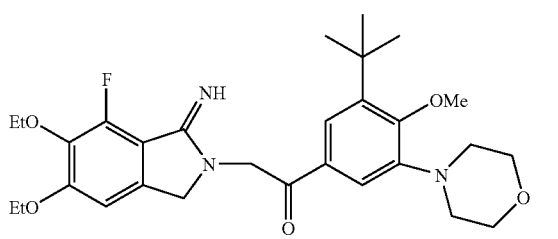

or a salt thereof;

dissolving the compound represented by formula (XIII)), or the salt thereof, in a mixed solvent comprising an alcohol and water, or a mixed solvent comprising an ether and water; and after dissolution, adding additional water to precipitate crystals of the compound represented by formula (XIII)), or the salt thereof, (In the above formulas, Me represents a methyl group, and Et represents an ethyl group);

[17] a method for recrystallizing a cyclic benzamidine derivative (C), wherein the method comprises the steps of dissolving a compound represented by formula (XIII)

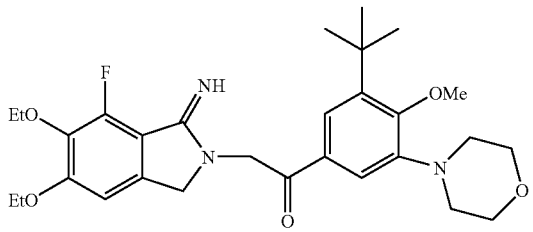

(wherein, Me represents a methyl group, and Et represents an ethyl group)), or the salt thereof, in a mixed solvent comprising an alcohol and water, or a mixed solvent comprising an ether and water; and after dissolution, adding additional water to precipitate crystals of the compound represented by formula (XIII)), or the salt thereof;

[18] the recrystallization method of [17], wherein the mixed solvent is a mixed solvent comprising an alcohol and water;

[19] a compound represented by formula (XIV)

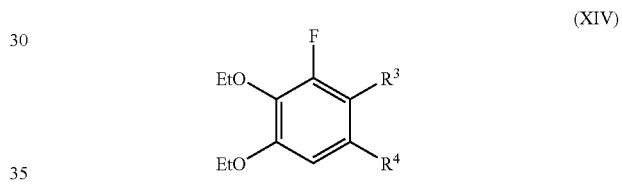

(wherein, $R^3$ represents a halogen atom or CN; $R^4$ represents a hydrogen atom, a methyl group, —CHO, —CH$_2$OH, —CH$_2$Hal (wherein, Hal represents a halogen atom), —CH$_2$—OSO$_2$R$^1$ (wherein, R$^1$ represents a $C_{1-6}$ alkyl group, a halogenated $C_{1-6}$ alkyl group, a $C_{6-10}$ aryl group, or a halogenated $C_{6-10}$ aryl group), a phthalimide methyl group, or a succinimide methyl group; and Et represents an ethyl group);

[20] a compound represented by formula (XV)

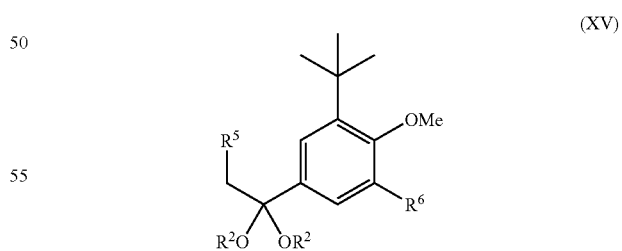

(wherein, each of the two $R^2$s represents an alkyl group of 1-4 carbon atoms, and the two $R^2$s may be bonded to each other to form a cyclic group represented by —(CH$_2$)$_n$— (wherein, n represents an integer of 2 to 4); $R^5$ represents a hydrogen atom or a halogen atom, $R^6$ represents a halogen atom or a morpholino group, and Me represents a methyl group), or a salt thereof;

[21] a method for producing cyclic benzamidine derivative (C), wherein the method comprises
producing the fluorinated cyclic benzamidine derivative (A) represented by formula (II)

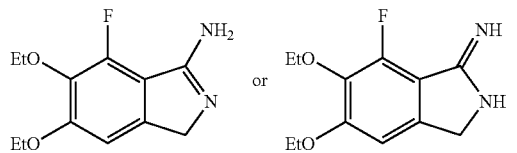

or a salt thereof, by the method of any one of [1] to [10], and
reacting the obtained fluorinated cyclic benzamidine derivative (A) or a salt thereof with the morpholine-substituted phenacyl derivative (B) represented by formula (VIII)

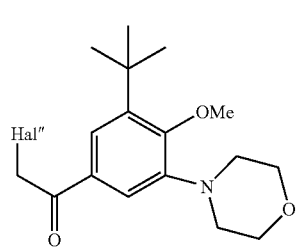

(wherein, Hal" represents a halogen atom) or a salt thereof to obtain the compound represented by formula (XIII)

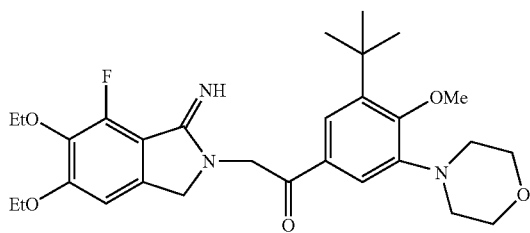

or a salt thereof
(in the formulas, Et represents an ethyl group, and Me represents a methyl group);
[22] a method for producing cyclic benzamidine derivative (C), wherein the method comprises
producing the morpholine-substituted phenacyl derivative (B) represented by formula (VIII)

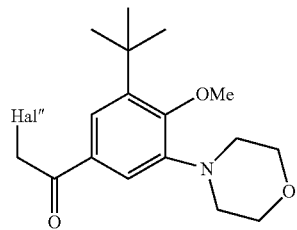

(wherein, Hal" represents a halogen atom) or a salt thereof by the method of [11] or [12], and
reacting the obtained morpholine-substituted phenacyl derivative (B) or the salt thereof with the fluorinated cyclic benzamidine derivative (A) represented by formula (II)

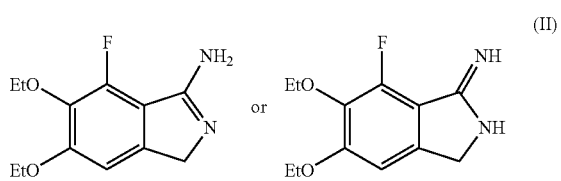

or a salt thereof to obtain the compound represented by formula (XII)

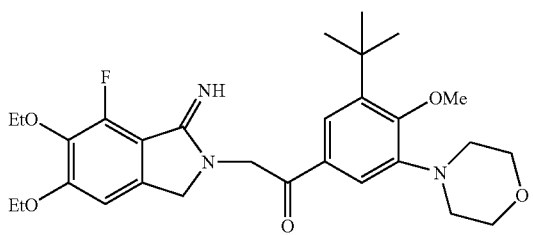

(in the formulas, Et represents an ethyl group, and Me represents a methyl group); and
[23] a method for producing cyclic benzamidine derivative (C), wherein the method comprises
producing the fluorinated cyclic benzamidine derivative (A) represented by formula (II)

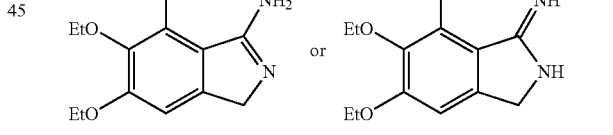

or a salt thereof by the method of any one of [1] to [10];
producing the morpholine-substituted phenacyl derivative (B) represented by formula (VIII)

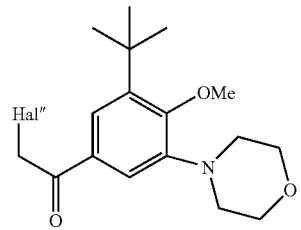

(wherein, Hal" represents a halogen atom) or a salt thereof by the method of [11] or [12], and reacting the fluorinated cyclic benzamidine derivative (A) or a salt thereof with the morpholine-substituted phenacyl derivative (B) or a salt thereof, to obtain the compound represented by formula (XIII)

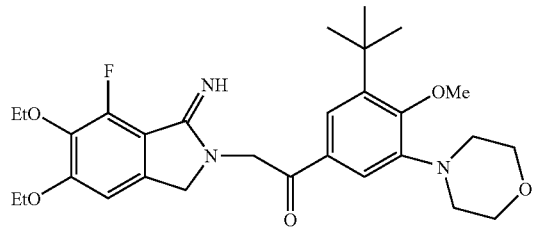

(XIII)

or a salt thereof (in the formulas, Et represents an ethyl group, and Me represents a methyl group).

Unless stated otherwise, "Me" represents a methyl group and "Et" represents an ethyl group in this description.

The methods of the present invention for producing a cyclic benzamidine derivative (C) involve a coupling reaction between a fluorinated cyclic benzamidine derivative (A) and a morpholine-substituted phenacyl derivative (B). The following describes the respective methods for producing the fluorinated cyclic benzamidine derivative (A) and the morpholine-substituted phenacyl derivative (B), and the reaction of coupling these derivatives.

<Fluorinated Cyclic Benzamidine Derivative (A)>

Production of the Fluorinated Cyclic Benzamidine Derivative (A)

The methods of the present invention for producing the fluorinated benzamidine derivative (A) represented by formula (II)

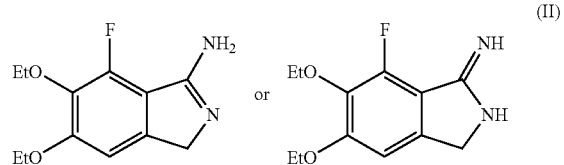

(II)

(hereinafter, sometimes referred to as "compound (II)"), or a salt thereof, comprise the step of reacting a compound represented by formula (I) with an ammonia or an imide

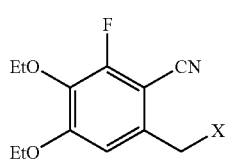

(I)

hereinafter, sometimes referred to as "compound (I)").

The fluorinated benzamidine derivative (A) may exist as a tautomer having two structures.

This fluorinated benzamidine derivative (A) (compound (II)) may exist as a salt thereof.

Herein, there are no particular limitations as to the type of salt, as long as it is a pharmaceutically acceptable salt formed with a compound of the present invention. Examples of such salts include preferably hydrogen halide salts (for example, hydrofluoride salts, hydrochloride salts, hydrobromide salts, hydroiodide salts, etc.), inorganic acid salts (for example, sulfuric acid salts, nitric acid salts, perchloric acid salts, phosphoric acid salts, carbonic acid salts, bicarbonic acid salts, etc.), organic carbonic acid salts (for example, acetic acid salts, trifluoroacetic acid salts, oxalic acid salts, maleic acid salts, tartaric acid salts, fumaric acid salts, citric acid salts, etc.), organic sulfonic acid salts (for example, methanesulfonic acid salts, trifluoromethanesulfonic acid salts, ethanesulfonic acid salts, benzenesulfonic acid salts, toluenesulfonic acid salts, camphorsulfonic acid salts, etc.), and amino acid salts (for example, aspartic acid salts, glutamic acid salts, etc.), and more preferably, hydrochloric acid salts, hydrobromic acid salts, sulfuric acid salts, phosphoric acid salts, acetic acid salts, maleic acid salts, tartaric acid salts, fumaric acid salts, citric acid salts, and methanesulfonic acid salts.

Salts formed with the compounds represented by formulas (I), (I'), (I"), (III) to (XVII) shown below are examples of those similar to the salts of the fluorinated benzamidine derivative (A).

Even when the phrase "compound or a salt thereof" is not clearly indicated in this description, compounds represented by formulas (I), (I'), (I"), (II) to (XVII), or compounds (I), (I'), (I"), (II) to (XVII) may include the salts of the compounds.

In formula (I), X represents a leaving group, and examples of the leaving group include —OSO$_2$R$^1$, a halogen atom, or such.

R$^1$ represents a C$_{1-6}$ alkyl group, a halogenated C$_{1-6}$ alkyl group, a C$_{6-10}$ aryl group, or a halogenated C$_{6-10}$ aryl group.

As used herein, the term "C$_{1-6}$ alkyl group" is a monovalent group derived by removing any one hydrogen atom from an aliphatic hydrocarbon of 1-6 carbon atoms, and refers to a linear or branched alkyl group of 1-6 carbon atoms. Specific examples include a methyl group, an ethyl group, a propyl group, an isopropyl group, a butyl group, an isobutyl group, an s-butyl group, a t-butyl group, a pentyl group, an isopentyl group, a 2-methylbutyl group, a neopentyl group, a 1-ethylpropyl group, a hexyl group, a 4-methylpentyl group, a 3-methylpentyl group, a 2-methylpentyl group, a 1-methylpentyl group, a 3,3-dimethylbutyl group, a 2,3-dimethylbutyl group, and a 2-ethylbutyl group. Among them, examples are preferably an alkyl group of 1-4 carbon atoms (a C$_{1-4}$ alkyl group), and more preferably a methyl group and an ethyl group.

As used herein, the term "C$_{6-10}$ aryl group" means an aromatic cyclic hydrocarbon group of 6 to 10 carbon atoms. Specific examples include a phenyl group, a tolyl group, a naphthyl group, and such. Among them, a tolyl group is preferable, and a p-tolyl group is more preferable.

As used herein, the term "halogenated C$_{1-6}$ alkyl group" means a group in which a hydrogen atom in the "C$_{1-6}$ alkyl group" defined above is substituted with a halogen atom. Specific examples include a trifluoromethyl group.

As used herein, the term "halogenated C$_{6-10}$ aryl group" means a group in which a hydrogen atom in the "C$_{6-10}$ aryl group" defined above is substituted with a halogen atom.

Specific examples include a p-bromophenyl group and such.

As used herein, examples of a "halogen atom" include a bromine atom, a chlorine atom, and an iodine atom. The halogen atom in the leaving group X is preferably a bromine atom.

More specifically, examples of —$OSO_2R^1$ containing this type of $R^1$ include a methanesulfonyl group (a mesyl group or an Ms group), a trifluoromethanesulfonyl group (a trifl group or a Tf group), a p-toluenesulfonyl group (a tosyl group or a Ts group), a p-bromobenzenesulfonyl group (a brosyl group or a Bs group), and such. Among them, a methanesulfonyl group or a p-toluenesulfonyl group is preferable, and a methane sulfonyl group is more preferable.

The "imide" refers to a compound in which two hydrogen atoms of an ammonia are substituted with acyl groups, and is a compound having a structure represented by "—CON-HCO—". Preferred examples include cyclic imides, and among cyclic imides, preferable examples include phthalimide and succinimide.

Depending on the reaction conditions, examples of "ammonia" include ammonia gas, liquid ammonia, or an ammonia solution in which gaseous or liquid ammonia is dissolved in water or an organic solvent such as alcohol at an arbitrary concentration. The preferred examples among these are ammonia gas and liquid ammonia. A detailed description will follow.

(Methods for Preparing (A) or a Salt Thereof With X Being —$OSO_2R^1$ or a Halogen Atom When Ammonia is Used)

Specifically, the preferred methods for producing the fluorinated benzamidine derivative (A) (compound (II)) or a salt thereof by reacting the aforementioned compound (I) with ammonia ($NH_3$) include the method of reacting with $NH_3$ a compound represented by formula (I') shown below (hereinafter, referred to as compound (I') in some cases), which is compound (I) comprising —$OSO_2R^1$ as X; alternatively, reacting with $NH_3$ the compound represented by formula (I") shown below (hereinafter, referred to as "compound (I") in some cases), which is compound (I) comprising a halogen atom for X. In formula (I') and formula (I"), Hal is a halogen atom, and $R^1$ has the same meaning as defined above.

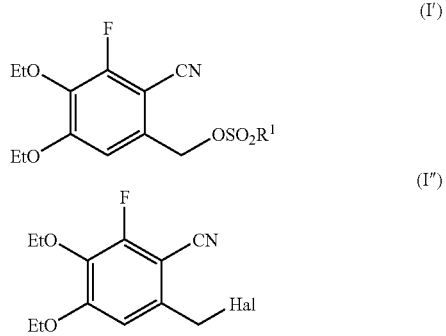

In this case, the reaction is generally carried out in a solvent in the presence of ammonia gas or liquid ammonia. The solvent is not particularly limited as long as it does not inhibit the reaction. For example, toluene; tetrahydrofuran (THF), diethyl ether, tert-butylmethyl ether, dioxane, methanol, ethanol, methylene chloride, 1,2-dimethoxyethane, and such may be used preferably, and more preferably toluene and 1,2-dimethoxyethane may be used. These solvents can be used individually or in combinations of two or more types of solvents.

The amount of ammonia used with respect to the aforementioned compound (I') or compound (I") is preferably 1 equivalent or more, and more preferably in the range of more than 1 equivalent and less than 10 equivalents.

When using ammonia gas, the reaction temperature is preferably in the range between −20° C. and 50° C., and more preferably in the range between 0° C. and 30° C. When using liquid ammonia, the temperature is preferably in the range between −20° C. and 30° C., and more preferably in the range between 0° C. and 20° C.

The reaction time is preferably 10 minutes to 24 hours, and more preferably 30 minutes to 12 hours.

(Methods for Preparing (A) or a Salt Thereof With X Being —$OSO_2R^1$ or a Halogen Atom When an Imide is Used)

Specifically, the preferred methods for producing the fluorinated benzamidine derivative (A) (compound (II)) or a salt thereof by reacting the aforementioned compound (I) with an imide includes the method of reacting the aforementioned compound (I') or compound (I") with an imide or a metal salt thereof.

The imide may be a phthalimide, a succinimide, or such, and the following shows an example in which phthalimide is used.

When using this reaction method, after the reaction of the aforementioned compound (I') or compound (I") with a phthalimide or a metal salt thereof, the method further comprises the step of converting the obtained 3,4-diethoxy-2-fluoro-6-(phthalimidemethyl)benzonitrile (hereinafter, referred to as compound (XVI) in some cases), represented by formula (XVI) shown below, into an amine derivative. Hal and $R^1$ have the same meanings as defined above.

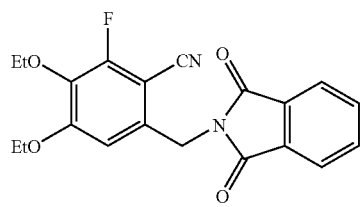

The reaction between phthalimide and compound (I') or compound (I") is generally performed in a solvent and in the presence of a base.

An appropriate choice of a solvent is one that does not inhibit the reaction. For example, amides such as N,N-dimethylformamide, N,N-dimethylacetamide, and N-methylpyrrolidone, and ethers such as THF, diethyl ether, tert-butylmethyl ether, and dioxane may be preferably used.

These solvents can be used individually or in combinations of two or more types of solvents, and is preferably an amide-ether mixture. The use of a mixture suppresses the generation of by-products, and increases the reaction yield.

For the base, tert-butoxide of an alkali metal such as potassium tert-butoxide, and sodium tert-butoxide, alkali metal $C_{1-4}$ alkoxide such as sodium methoxide, and sodium ethoxide, and such may be used. Among them, preferably tert-butoxide of an alkali metal, and more preferably potassium tert-butoxide is used. Examples of phthalimide metal salts include metal salts derived from these bases.

The amount of phthalamide used with respect to compound (I') or compound (I") is preferably 1 equivalent or more, and more preferably in the range of more than 1 equivalent and less than 1.3 equivalents. The amount of base used with respect to compound (I') or compound (I") is preferably 1 equivalent or more, and more preferably in the range of more than 1 equivalent and less than 1.5 equivalents.

The reaction temperature is preferably from 0° C. to the boiling point of a solvent, and more preferably in the range between room temperature and the boiling point of a solvent. The reaction time is preferably 10 minutes to 24 hours, and more preferably 30 minutes to 10 hours.

Specifically, conversion of compound (XVI) to an amine derivative can be performed by, for example, performing a hydrazine degradation.

Generally, the hydrazine degradation is performed in a solvent by reacting hydrazine or hydrazine hydrate with compound (XVI), and this is followed by treatment with an acid when necessary.

An appropriate choice of a solvent is one that does not inhibit the reaction. For example, amides such as N,N-dimethylformamide, N,N-dimethylacetamide, and N-methylpyrrolidone, ethers such as diethyl ether, diisopropyl ether, ethyleneglycol dimethylether, tetrahydrofuran, tert-butylmethylether, and dioxane, and alcohols such as methanol, and ethanol may be preferably used.

These solvents can be used individually or in combinations of two or more types of solvents.

For the acid treatment, hydrochloric acid, sulfuric acid, or such may be used.

The amount of hydrazine or hydrazine hydrate used with respect to compound (XVI) is preferably 1 equivalent or more, and more preferably, 1 equivalent or more and 3 equivalents or less.

The reaction temperature is preferably –20° C. to the boiling point of a solvent, and more preferably in the range between room temperature and the boiling point of a solvent. The reaction time is preferably 10 minutes to 24 hours, and more preferably 30 minutes to 10 hours.

After compound (XVI) is converted into an amine derivative in this manner, a neutralization procedure is performed as necessary using a base such as sodium hydroxide to cause intramolecular ring formation to obtain the fluorinated benzamidine derivative (A) (compound (II)) or a salt thereof.

Production of Compound (I')

Compound (I') represented by formula (I')

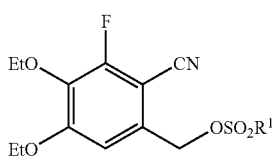

(wherein, $R^1$ represents a $C_{1-6}$ alkyl group, a halogenated $C_{1-6}$ alkyl group, a $C_{6-10}$ aryl group, or a halogenated $C_{6-10}$ aryl group) can be obtained by reacting the compound represented by formula (III)

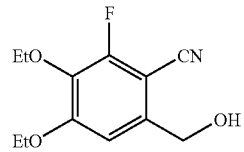

(hereinafter, referred to as compound (III) in some cases) with $R^1SO_2Y$ or $(R^1SO_2)_2O$.

In formula (I'), $R^1$ has the same meaning as defined above. The $R^1$ of $R^1SO_2Y$ or $(R^1SO_2)_2O$, which is a raw material for compound (I'), has the same meaning as the $R^1$ in compound (I'). Y is a halogen atom. Examples of the halogen atom include a bromine atom, a chlorine atom, and an iodine atom. Among them, chlorine atom is preferred.

Specific examples of $R^1SO_2Y$ include methanesulfonyl chloride (MsCl), p-toluenesulfonyl chloride (TsCl), trifl chloride (TfCl), brosyl chloride (BsCl), and such.

Specifically, examples of $(R^1SO_2)_2O$ contain a mesyl group, a tosyl group, a trifl group, or a brosyl group, and include sulfonic acid anhydrides such as trifluoromethanesulfonic acid anhydride.

The reaction between compound (III) and $R^1SO_2Y$ or $(R^1SO_2)_2O$ is generally performed in a solvent in the presence of a base.

The solvent is not particularly limited as long as it does not inhibit the reaction. Examples include ethers such as 1,2-dimethoxyethane, tetrahydrofuran, and dioxane, aromatic hydrocarbons such as toluene and xylene, and halogenated hydrocarbons such as methylene chloride. 1,2-dimethoxyethane is preferable.

The base that may be used is preferably a triethylamine, a pyridine, or a diisopropylethyl amine, and more preferably a triethylamine.

The amount of $R^1SO_2Y$ or $(R^1SO_2)_2O$ used with respect to compound (III) is preferably 1 equivalent or more, and more preferably 1 equivalent or more and 1.3 equivalents or less.

The reaction temperature is preferably in the range between –20° C. and 40° C., and more preferably in the range between 0° C. and 30° C. The reaction time is preferably 10 minutes to 24 hours, and more preferably 30 minutes to 10 hours.

Production of Compound (I")

Compound (I") represented by formula (I")

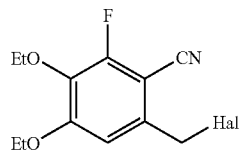

(wherein, Hal represents a halogen atom) can be obtained by reacting compound (III) represented by formula (III) with a halogenating reagent.

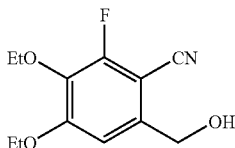

(III)

In formula (I''), Hal represents a halogen atom, such as bromine atom, a chlorine atom, and an iodine atom, and among them, a bromine atom is preferred.

An appropriate choice of a halogenating reagent is one that can be used for halogenation of a hydroxyl group. Examples of such a halogenating reagent include N-chlorosuccinimide, N-bromosuccinimide, N-iodosuccinimide, chlorine, bromine, iodine, thionyl chloride, thionyl bromide, sulfuryl chloride, oxalyl chloride, phosphorus oxychloride, phosphorus oxybromide, phosphorus pentachloride, phosphorus tribromide, methanesulfonyl chloride, p-toluenesulfonyl chloride, and such. Furthermore, combinations of triphenylphosphine with N-chlorosuccinimide, N-bromosuccinimide, N-iodosuccinimide, chlorine, bromine, iodine, or such may be used. Among them, phosphorus tribromide is preferred.

The reaction between compound (III) and a halogenating reagent is generally performed in a solvent.

The solvent is not particularly limited as long as it does not inhibit the reaction. Examples include ethers such as 1,2-dimethoxyethane, tetrahydrofuran, diethylether, tert-butylmethylether, and dioxane, aromatic hydrocarbons such as toluene and xylene. A preferable example is 1,2-dimethoxyethane.

The solvents can be used individually or in combinations of two or more types of solvents.

The amount of a halogenating reagent used with respect to compound (III) is preferably 1.2 equivalents or more, and more preferably 1.5 equivalents or more and 3 equivalents or less.

The reaction temperature is preferably in the range between −20° C. and 40° C., and more preferably in the range between 0° C. and 30° C. The reaction time is preferably 10 minutes to 12 hours, and more preferably 30 minutes to 10 hours.

Furthermore, compound (I'') can be obtained by reacting the compound represented by formula (IV) with a halogenating reagent.

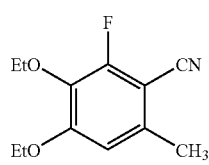

(IV)

Examples of the halogenating reagent in this case include N-bromosuccinimide (NBS), N-iodosuccinimide, N-chlorosuccinimide, chlorine, bromine, iodine, and such.

The reaction between compound (IV) and the halogenating reagent is generally performed in a solvent in the presence of a radical reaction initiator.

The solvent is not particularly limited as long as it does not inhibit the reaction. Examples include halogens such as carbon tetrachloride, chlorobenzene, and α,α,α-trifluorotoluene. The solvents can be used individually or in combinations of two or more types of solvents.

The radical reaction initiator is not particularly limited, and a standard radical reaction initiator may be used. Examples include azo compounds such as 2,2'-azobisisobutyronitrile (AIBN), and peroxides such as benzoyl peroxide. 2,2'-azobisisobutyronitrile (AIBN) is preferred.

The halogenating reagent used with respect to compound (IV) is preferably 1 equivalent or more, and more preferably 1 equivalent or more and 1.5 equivalent or less.

The reaction temperature is preferably in the range between room temperature and the boiling point of a solvent. The reaction time is preferably 10 minutes to 24 hours, and more preferably 30 minutes to 10 hours.

Production of Compound (III)

The compound represented by formula (III) can be obtained by steps comprising (1) to (3) described below:

(1) Step 1: reacting the compound represented by formula (V)

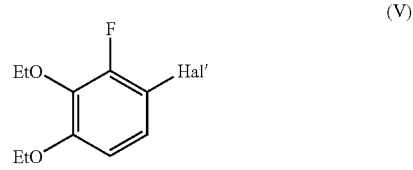

(V)

(wherein, Hal' represents a halogen atom) (hereinafter, referred to as compound (V) in some cases) with a cyanation reagent to obtain the compound represented by formula (VI)

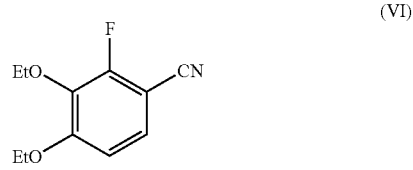

(VI)

(hereinafter, referred to as compound (VI) in some cases);

(2) Step 2: obtaining the compound represented by formula (VII)

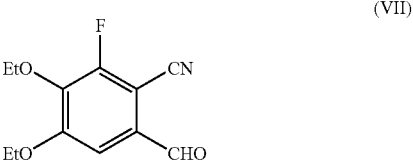

(VII)

(hereinafter, referred to as compound (VII) in some cases) through a formylation reaction of the compound represented by formula (VI)); and (3) Step 3: obtaining the compound represented by formula (III)

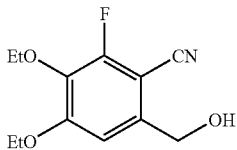

(compound (III)) by reducing the compound represented by formula (VII)).

Hereinafter, each of the steps will be described individually.

(Step 1: Compound (V)→Compound (VI))

Compound (VI) can be obtained by reacting compound (V) with a cyanation reagent.

Examples of the halogen atom in compound (V) include a bromine atom, chlorine atom, and iodine atom, and among them, bromine atom is preferred.

Examples of the cyanation reagent include copper (I) cyanide, potassium cyanide, sodium cyanide, zinc cyanide and such. Copper (I) cyanide is preferred.

The reaction between compound (V) and the cyanation reagent is generally performed in a solvent.

The solvent is not particularly limited as long as it does not inhibit the reaction, but since a high reaction temperature may be required for cyanation, a solvent that has a high boiling point and sufficiently dissolves the cyanation reagent is preferred. Examples of such solvents include amides such as N,N-dimethylformamide (DMF), and 1-methyl-2-pyrolidine, and ureas such as 1,3-dimethyl-2-imidazolidinone. Among them, DMF can be preferably used.

These solvents can be used individually or in combinations of two or more types of solvents.

The amount of cyanation reagent used with respect to compound (V) is preferably 1 to 5 equivalents, and more preferably 1 to 2 equivalents.

The reaction temperature is preferably in the range between 100 and 200° C. The reaction time is preferably 10 minutes to 24 hours, and more preferably 30 minutes to 10 hours.

Compound (V) which is the raw material for synthesizing compound (III) can be obtained by halogenating the compound of formula (XVII) (hereinafter referred to as compound (XVII) in some cases).

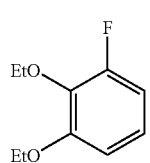

Halogenation can be performed by reacting compound (XVII) with a halogenating reagent in a solvent.

Examples of the halogenating reagent include N-bromosuccinimide (NBS), N-iodosuccinimide, N-chlorosuccinimide, chlorine, bromine, iodine, and such, and an appropriate reagent may be used for the desired halogenated compound.

The preferred reagent is N-bromosuccinimide.

The solvent is not particularly limited as long as it does not inhibit the reaction. Examples include nitriles such as acetonitrile, ethers such as diethyl ether, diisopropylether, ethyleneglycol dimethylether, tetrahydrofuran, tert-butylmethyl ether, and dioxane, esters such as ethyl acetate and methyl acetate, amides such as N,N-dimethylformamide, N,N-dimethylacetamide, 1-methyl-2-pyrolidinone, 1,3-dimethyl-2-imidazolidinone, and such may be used preferably, and acetonitrile is more preferred.

These solvents can be used individually or in combinations of two or more types of solvents.

The amount of the halogenating reagent used with respect to compound (XVII) is preferably in the range of 0.95 to 1.2 equivalents.

The reaction temperature for example, is preferably in the range between −10° C. and room temperature. The reaction time is preferably approximately 10 minutes to 24 hours.

Compound (XVII) can be obtained by, for example, forming a diethyl ether compound of a commercially available 1,2-dihydroxy-3-fluorobenzene.

(Step (2): Compound (VI)→Compound (VII))

Compound (VII) can be obtained by formylating compound (VI).

Examples of the formylation method include the method of anionizing compound (VI) in a solvent with a base and reacting with a formylation reagent, or the method that uses a Vilsmeier reagent, and such.

The following describes the method of anionizing compound (VI) with a base and reacting with a formylation reagent.

In the case of anionizing compound (VI) in a solvent with a base and reacting with a formylation reagent, the solvent can be any solvent as long as it does not inhibit the reaction. For example, hydrocarbons such as n-hexane, n-heptane, benzene, toluene, and xylene, ethers such as diethylether, diisopropylether, 1,2-dimethoxyethane, tetrahydrofuran, and dioxane, and such may be used preferably, and more preferred are n-heptane and tetrahydrofuran. These solvents may be used individually or in combinations of two or more types of solvents.

When anionizing compound (VI) with a base, if n-heptane is included as a solvent, compound (VI) comprising a lithiated position 6 will precipitate as crystals in the reaction system, and can further stabilize the existence of active species.

For the base, alkyl alkali metal, metal amide, and such may be used preferably. Examples of the alkyl alkali metal include N-butyl lithium, sec-butyl lithium, tert-butyl lithium, phenyl lithium, methyl lithium, and such. Examples of the metal amide include lithium diisopropylamide, lithium 2,2,6,6-tetramethylpiperidide, lithium hexamethyldisilazide, sodium hexamethyldisilazide, and such. Among them, metal amides can be preferably used, and lithium 2,2,6,6-tetramethylpiperidide is more preferable.

Examples of the formylation reagent include N,N-dimethylformamide, N-formylmorpholine, and such.

The amount of base used with respect to compound (VI) is preferably 1 equivalent or more, and more preferably 1 equivalent or more and 2 equivalents or less.

The amount of the formylation reagent used with respect to compound (VI) is preferably 1 equivalent or more, and more preferably 1 equivalent or more and 3 equivalents or less.

The metal amide can be prepared in a reaction vessel by treating an amine reagent such as 2,2,6,6-tetramethylpiperidine (TMP) with an alkyl alkali metal such as n-butyl lithium, sec-butyl lithium, tert-butyl lithium, methyl lithium, phenyl lithium, and such, as necessary. In this case, the preferred combination is 2,2,6,6-tetramethylpiperidine and n-butyl lithium.

The amount of amine reagent such as 2,2,6,6-tetramethylpiperidine used with respect to the alkyl alkali metal is preferably 1-2 equivalents or less, and more preferably in the range of 1.01-1.5 equivalents. By adding a small excess of an amine reagent such as TMP to the base, formylation can be carried out in good yield.

The reaction temperature at the anion formation stage is not limited, and differs depending on the type of base used. For example, it is preferably in the range of −100° C. to room temperature. The reaction time for anion formation is preferably 10 minutes to 12 hours.

The reaction temperature at the formylation stage is preferably in the range of −100° C. to room temperature. The reaction time for formylation is preferably 10 minutes to 24 hours, and more preferably 30 minutes to 10 hours.

After the formylation reaction, quenching was performed with an acid such as acetic acid, hydrochloric acid, or sulfuric acid. Among them, the use of acetic acid is preferred. By using acetic acid, compound (VII) can be precipitated and obtained as crystals while reducing the amount of impurities.

(Step (3): Compound (VII)→Compound (III))

Compound (III) can be obtained by reducing the aforementioned compound (VII) in a solvent. Various reducing agents can be used for the reduction.

Examples of a reducing agent include sodium triacetoxyborohydride, sodium borohydride, lithium borohydride, sodium cyanoborohydride, lithium aluminum hydride, combinations of sodium borohydride and acetic acid, and such. Among them, the use of sodium triacetoxyborohydride is preferred.

The solvent can be any solvent as long as it does not inhibit the reaction. Depending on the type of reducing agent, for example, esters such as ethyl acetate, and methyl acetate, amides such as N,N-dimethylformamide, N,N-dimethylacetamide, and N-methylpyrrolidone, ethers such as diethyl ether, diisopropyl ether, 1,2-dimethoxyethane, tetrahydrofuran, and dioxane, alcohols such as ethanol, and such can be used preferably. The use of tetrahydrofuran is more preferable.

These solvents can be used individually or in combinations of two or more types of solvents.

The amount of reducing agent used with respect to compound (VII) is preferably 1 equivalent or more, and more preferably 1 equivalent or more and 3 equivalents or less.

For example, the reaction temperature is preferably in the range between 0° C. and 100° C. The reaction time is preferably 10 minutes to 24 hours, and more preferably 30 minutes to 10 hours.

Production of Compound (I″)

Compounds represented by formula (I″) shown below can be obtained by performing steps comprising (1″) to (3″) described below.

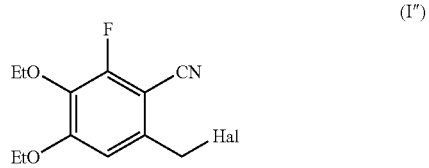

In formula (I″), Hal represents a halogen atom. Examples of the halogen atom are a bromine atom, a chlorine atom, and an iodine atom, and among them, a bromine atom is preferred.

Step (1′): The step of reacting compound (V) represented by formula (V)

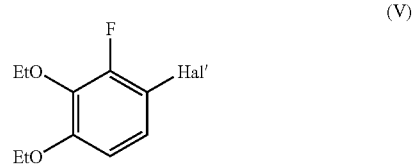

(wherein, Hal′ represents a halogen atom) with a cyanation reagent to obtain compound (VI) represented by formula (VI);

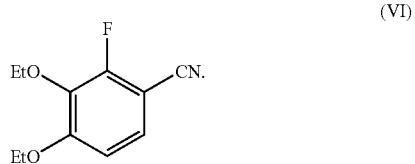

Step (2′): The step of obtaining a compound represented by formula (IV)

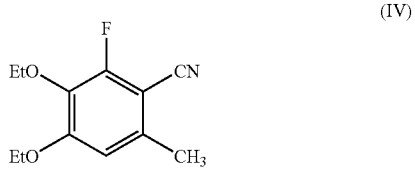

(hereinafter, referred to as compound (IV) in some cases) through methylation of the compound represented by formula (VI);

Step (3′): The step of obtaining the compound represented by formula (I″) by reacting the compound represented by formula (IV) with a halogenating reagent.

Each step will be described in detail below.

(Step (1′): Compound (V)→Compound (VI))

Step (1′) is identical to the aforementioned Step (1).

(Step (2′): Compound (VI)→Compound (IV))

Compound (IV) can be obtained by methylating compound (VI). The method of methylation is not particularly limited and include, for example, a method of reacting compound (VI) with a methylation reagent in a solvent under the presence of a base.

Examples of the methylation reagent include methyl halides such as methyl iodide, dimethylsulfate, methyl methanesulfonate and such, and methyl iodide is preferred.

For the base, an alkyl alkali metal, a metal amide, or such can be used. Examples of an alkyl alkali metal include methyl lithium, n-butyl lithium, sec-butyl lithium, tert-butyl lithium, phenyl lithium and such, and examples of a metal amide include lithium diisopropylamide, lithium 2,2,6,6-tetramethylpiperidide, lithium hexamethyldisilazide, sodium hexamethyldisilazide and such. Among them, the use of a metal amide is preferable, and more preferred is lithium 2,2,6,6-tetramethylpiperidide.

Metal amides can be prepared in a reaction vessel by treating an amine reagent such as 2,2,6,6-tetramethylpiperidine (TMP) with an alkyl alkali metal such as methyl lithium, n-butyl lithium, sec-butyl lithium, tert-butyl lithium, and phenyl lithium, as necessary. The combination of 2,2,6,6-tetramethylpiperidine and methyl lithium is preferable.

The solvent can be any solvent that does not inhibit the reaction. For example, hydrocarbons such as n-hexane, n-heptane, benzene, toluene, and xylene, and ethers such as diethyl ether, diisopropyl ether, 1,2-dimethoxyethane, tetrahydrofuran, and dioxane may be preferably used, and the use of ethers such as tetrahydrofuran is preferable. These solvents can be used individually or in combinations of two or more types of solvents.

The amount of base used with respect to compound (VI) is preferably 1 equivalent or more, and more preferably 1 to 1.5 equivalents.

The amount of methylation reagent used with respect to compound (VI) is preferably 1 equivalent or more, and more preferably 1 equivalent or more and 2 equivalents or less.

The amount of an amine reagent such as TMP used is preferably equivalent to the amount of base.

The reaction temperature at the anion formation stage is not limited and differs depending on the type of base used, and for example, is preferably in the range of −100° C. to room temperature. The reaction time for anion formation is preferably 10 minutes to 12 hours.

The methylation step is preferably performed at a temperature in the range of −100° C. to room temperature. The reaction time for methylation is preferably 10 minutes to 12 hours, and more preferably 30 minutes to 10 hours.

(Step (3'): Compound (IV)→Compound (I"))

Step (3') is identical to that described above.

The methods for producing a fluorinated benzamidine derivative (A) (compound (II)) or a salt thereof such as in the present invention give a good yield at each step and have excellent reproducibility. Furthermore, since purification of the products obtained at each step by column chromatography and such is not required, they are industrially very useful. Furthermore, in Patent Document 1, for example, the fluorinated benzamidine derivative (A) (compound (II)) is obtained via catalytic reduction of an ortho-dicyano intermediate using platinum oxide as a catalyst. However, the methods of the present invention do not use a catalyst, and therefore, purification of this catalyst is unnecessary. Further, these methods are very safe as there is no fear of ignition caused by catalysts after purification. Therefore, the methods are extremely useful for the production of the cyclic benzamidine derivative (C) (compound (XIII)).

Compound (XIV)

The compound of the present invention is represented by formula (XIV)

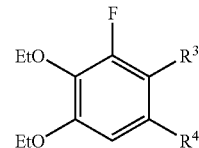

(wherein, $R^3$ represents a halogen atom or CN, $R^4$ represents a hydrogen atom, a methyl group, —CHO, —CH$_2$OH, —CH$_2$Hal (wherein, Hal represents a halogen atom), —CH$^2$—OSO$_2$R$^1$ (wherein, $R^1$ represents a C$_{1-6}$ alkyl group, a halogenated C$_{1-6}$ alkyl group, a C$_{6-10}$ aryl group, or a halogenated C$_{6-10}$ aryl group), phthalimide methyl group, or succinimide methyl group). The compound represented by formula (XIV) may be referred to as "compound (XIV)".

Specific examples of compound (XIV) include the following compounds, which are all novel compounds.

(Compound (I'))

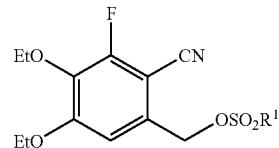

In formula (I'), $R^1$ has the same meaning as defined above.

(Compound (I"))

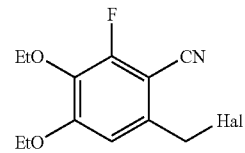

In formula (I"), Hal has the same meaning as defined above.

(Compound (III)) (3,4-diethoxy-2-fluoro-6-hydroxymethyl-benzonitrile)

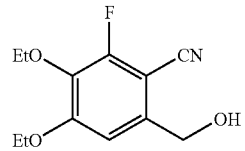

(Compound (IV)) (3,4-diethoxy-2-fluoro-6-methylbenzonitrile)

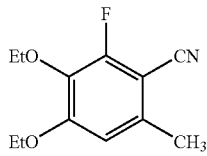

(Compound (V))

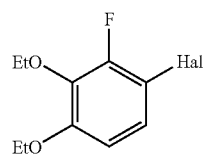

In formula (V), Hal represents a halogen atom, and examples of the halogen atom include a bromine atom, a chlorine atom, and an iodine atom.

(Compound (VI)) (3,4-diethoxy-2-fluorobenzonitrile)

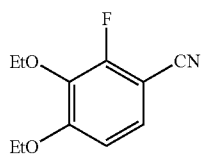

(Compound (VII)) (3,4-diethoxy-2-fluoro-6-formylbenzonitrile)

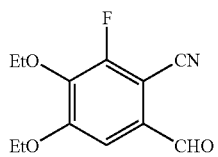

(Compound (XVI)) (3,4-diethoxy-2-fluoro-6-(phthalimidemethyl)benzonitrile)

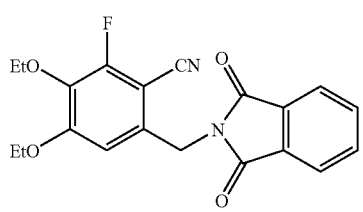

(Compound (XVIII)) (3,4-diethoxy-2-fluoro-6-(succinimidemethyl)benzonitrile)

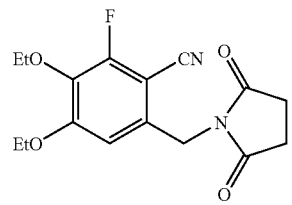

These compounds may serve as an intermediate in the production of fluorinated cyclic benzamidine derivative (A) or a salt thereof.

<Morpholine-Substituted Phenacyl Derivative (B)>

Production of the Morpholine-Substituted Phenacyl Derivative (B)

The method of the present invention for producing the compound represented by formula (VIII)

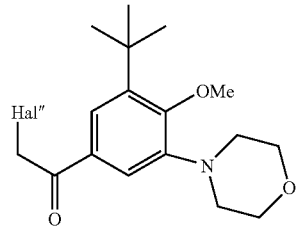

(hereinafter, it may be referred to as "morpholine-substituted phenacyl derivative (B)" or compound (VIII)) or a salt thereof comprises the steps of (1") to (3") described below. In formula (VIII), Hal" represents a halogen atom.

Step (1"): The step of reacting with morpholine the compound represented by formula (IX)

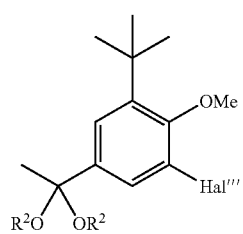

[wherein, each of the two $R^2$s represents a $C_{1-4}$ alkyl group (alkyl group of 1 to 4 carbon atoms), and the two $R^2$s can be bonded to each other to form a cyclic group represented by —$(CH_2)_n$— (wherein, n represents an integer of 2 to 4); Hal''' represents a halogen atom] (hereinafter, referred to as "compound (IX)") to obtain the compound represented by formula (X)

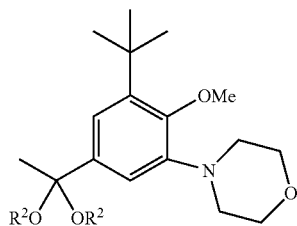

(wherein, R² represents the same group as in formula (IX)) (hereinafter, referred to as compound (X) in some cases);

Step (2"): The step of reacting the compound represented by formula (X) with a halogenating reagent to obtain the compound represented by formula (XI)

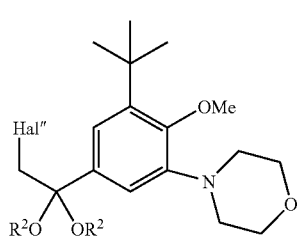

(wherein, R² represents the same group as in formula (IX), and Hal" represents a halogen atom) (hereinafter, referred to as compound (XI) in some cases));

Step (3"): The step of performing a deketalization reaction on the compound represented by formula (XI) to obtain the morpholine-substituted phenacyl derivative (B) represented by formula (VIII))

Each of the steps is described individually below.

(Step (1"): Compound (IX)→Compound (X))

Generally, compound (X) can be obtained by reacting compound (IX) with morpholine in a solvent under the presence of a base. In this case, a catalyst may be added.

In formula (IX), the halogen atom of Hal'" may be a bromine atom, a chlorine atom, an iodine atom, or such, and among them, a bromine atom is preferred.

Examples of the $C_{1-4}$ alkyl group of R² in formula (IX) include a methyl group, an ethyl group, an n-propyl group, an isopropyl group, an n-butyl group, a sec-butyl group, a tert-butyl group, and such. Among them, a methyl group is preferred. Furthermore, two R²s may bond with each other to form a cyclic ketal group represented by —$(CH_2)_n$— (wherein, n represents an integer of 2 to 4), and in this case n is preferably 2 or 3.

Examples of the base include alkali metal tert-butoxides such as potassium tert-butoxide, and sodium tert-butoxide; potassium carbonate, sodium carbonate, cesium carbonate, triethylamine, and such. Among them, sodium tert-butoxide is preferably used.

The solvent is not particularly limited and can be any solvent that does not inhibit the reaction. Examples include ethers such as 1,2-dimethoxyethane, tetrahydrofuran, and dioxane, and aromatic hydrocarbons such as toluene, and xylene. Among them, the use of ethers such as 1,2-dimethoxyethane is desirable, and 1,2-dimethoxyethane is preferred. The use of 1,2-dimethoxyethane increases the reaction rate as well as the reaction yield.

These solvents can be used individually or in combinations of two or more types of solvents.

The catalyst differs depending on the solvent and such that are used, and is not particularly limited as long as the reaction is not inhibited. Examples of such a catalyst include palladium acetate, tetrakis(triphenylphosphine)palladium (0), palladium(II)chloride, tris(dibenzilideneacetone)dipalladium(0), and dichloro[1,1'-bis(diphenylphosphine)-ferrocene]palladium(0). As necessary, metal ligands such as 2,2'-bis(diphenylphosphino-1,1'-binaphthyl (BINAP), triphenylphosphine, and tri-tert-butylphosphine may be used. A preferred combination is palladium acetate and 2,2'-bis(diphenylphosphino-1,1'-binaphthyl (BINAP). BINAP can be in racemic form or chiral form.

The amount of morpholine used with respect to compound (IX) is preferably in the range of 1 to 1.5 equivalents.

The amount of base used with respect to compound (IX) is preferably in the range of 1 to 2 equivalents.

When using palladium acetate as the catalyst, the amount used is preferably 1 mol % or more, and more preferably 1 to 10 mol %.

When using BINAP as the metal ligand, the amount used is preferably 1.5 mol % or more, and more preferably 1.5 to 15 mol %. The effect of catalyst addition may not be available at less than 1.5 mol %.

The desirable reaction temperature is approximately in the range between 75 and 90° C. The reaction time is preferably 10 minutes to 24 hours.

(Step (2"): Compound (X)→Compound (XI))

Compound (XI) can be obtained by reacting compound (X) in a solvent with a halogenating reagent.

In formula (X), R² is the same as the R² of formula (IX).

The halogen atom in formula (XI) is identical to, for example, the halogen atom in formula (IX).

Examples of the halogenating reagent include phenyltrimethylammonium tribromide, pyridinium hydrogen tribromide and such, and among them, phenyltrimethylammonium tribromide can be preferably used.

Any solvent that does not inhibit the reaction may be used as the solvent. For example, ethers such as 1,2-dimethoxyethane, diethyl ether, diisopropylether, tetrahydrofuran, and dioxane; amides such as N,N-dimethylformamide, N,N-dimethylacetamide, and N-methylpyrrolidone; nitriles such as acetonitrile; and alcohols such as methanol, ethanol, and propanol may be preferably used. Among them, ethers are preferable, and tetrahydrofuran is preferred.

When using tetrahydrofuran as the solvent, and for example, phenyltrimethylammonium tribromide as the halogenating reagent, the quaternary salt ($PhMe_3N^+Br^-$) formed as a result of the reaction has low solubility in tetrahydrofuran, and thus can be precipitated out of the reaction system and easily removed by filtration and such.

These solvents can be used individually or in combinations of two or more types of solvents.

The amount of halogenating reagent used with respect to compound (X) is preferably 1 to 1.9 equivalents, and more preferably 1 to 1.2 equivalents.

The reaction temperature is preferably, for example, in the range between 0° C. and room temperature.

The reaction time is preferably approximately 10 minutes to 24 hours.

(Step (3"): Compound (XI)→Compound (VIII))

Compound (VIII) can be obtained by deketalization, which involves adding an aqueous sodium thiosulfate solution to an extract of compound (XI) obtained by the aforementioned reaction method, or to a resulting solution of this reaction. Furthermore, deprotection can be performed as desired by treatment with an acid such as hydrochloric acid, sulfuric acid, acetic acid, trifluoroacetic acid, or p-toluenesulfonic acid, pyridinium p-toluenesulfonate or trimethylsilyl iodide.

Production of Compound (IX)

Compound (IX) represented by formula (IX) is obtained by, for example, carrying out the steps of ketalizing the carbonyl group in the compound represented by formula (XII)

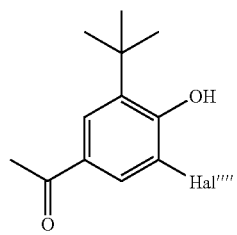

(XII)

(wherein, Hal'''' represents a halogen atom) (hereinafter, may be referred to as "compound (XII)") with $R^2OH$, $HC(OR^2)_3$, or $HO—(CH_2)_n—OH$ (wherein, $R^2$ has the same meaning defined above, and n represents an integer of 2 to 4), and methoxylating the hydroxyl group in the compound represented by formula (XII).

Examples of the halogen atom represented by Hal'''' include a chlorine atom, a bromine atom, and an iodine atom. Among them, a bromine atom is preferred.

Specific examples of the compounds represented by $R^2OH$ include methanol, ethanol, and such.

Specific examples of the compounds represented by $HC(OR_2)_3$ include trimethyl orthoformate, triethyl orthoformate, and such.

Examples of the methylation reagent used in the step of methoxylating the hydroxyl group include methyl iodide and such.

Ketalization of the carbonyl group is carried out in a solvent via reaction with $R^2OH$, $HC(OR^2)_3$, or $HO—(CH_2)_n—OH$ (wherein, n represents an integer of 2 to 4). A catalyst may be added in this case.

Examples of a catalyst include (±)-10-camphorsulfonic acid, hydrochloric acid, sulfuric acid, and p-toluenesulfonic acid and such. (±)-10-camphorsulfonic acid and p-toluenesulfonic acid are preferred.

Any solvent that does not inhibit the reaction may be used as the solvent in this case. For example, alcohols such as methanol, aromatic hydrocarbons such as benzene, toluene, and xylene, methylene chloride, and nitromethane may be used.

These solvents may be used individually or in combinations of two or more types of solvents.

When forming a cyclic ketal out of compound (IX) with the two $R^2$s bonded to each other, p-toluenesulfonic acid, ethylene glycol, and such may be added for the ketal formation.

The amount of $R^2OH$ or $HC(OR^2)_3$ used with respect to compound (XII) is preferably 3 equivalents or more, and more preferably approximately 3 to 10 equivalents.

The amount of catalyst used with respect to compound (XII) is preferably in the range of 1 to 4 mol %.

The reaction temperature during ketalization is preferably, for example, in the range between 0° C. and 60° C.

The reaction time is preferably 10 minutes to 24 hours or so.

Methoxylation reaction of the hydroxyl group can be performed in a solvent by adding a methyl halide such as methyl iodide. Addition of potassium carbonate, cesium carbonate, sodium methoxide, sodium ethoxide, potassium tert-butoxide, sodium tert-butoxide, and sodium hydride is preferable, and potassium carbonate is preferred.

For the solvent in methoxylation, any solvent that does not inhibit the reaction may be used. For example, ethers such as tetrahydrofuran, amides such as N,N-dimethylformamide, ketones such as acetone, nitriles such as acetonitrile, or methylene chloride may be used.

These solvents may be used individually or in combinations of two or more types of solvents.

The amount of methyl halide used with respect to compound (XII) is preferably 1 equivalent or more, and more preferably 1 to 3 equivalents or so.

When using potassium carbonate, the amount used with respect to compound (XII) is preferably 0.5 equivalents or more, and more preferably 1 to 3 equivalents or so.

The reaction temperature in methoxylation is not particularly limited, and is preferably, for example, in the range between 0° C. and 100° C. The reaction time is preferably 10 minutes to 12 hours or so.

The ketalization step and the methoxylation step can be separately performed, and the products from each step can be isolated and purified individually, without restricting the order of steps. Alternatively, methoxylation can be performed following ketalization without product isolation, or the ketalization can be performed following methoxylation without product isolation.

Production of Compound (XII)

Compound (XII) can be obtained via, for example, steps of reacting 2-tert-butylphenol with acetyl chloride to obtain 1-(3-tert-butyl-4-hydroxyphenyl)ethanone (Step (i)), and halogenating the obtained compound (Step (ii)).

A commercially available 2-tert-butylphenol may be used.

1-(3-tert-Butyl-4-hydroxyphenyl)ethanone can be obtained by, for example, reacting 2-tert-butylphenol with acetyl chloride in a solvent under the presence of a Lewis acid.

Any solvent that does not inhibit the reaction can be used as the solvent. For example, the use of an aromatic hydrocarbon such as benzene, toluene, or nitrobenzene, or carbon tetrachloride, is preferable. Among them, the use of toluene is preferred.

These solvents can be used individually or in combinations of two or more types of solvents.

For the Lewis acid, aluminum chloride, aluminum bromide, tin tetrachloride, and boron trifluoride may be used. Among them, aluminum chloride may be preferably used.

The amount of acetyl chloride used with respect to the raw material, 2-tert-butylphenol, is preferably 1 equivalent or more, and more preferably 1 to 3 equivalents or so.

The amount of Lewis acid used with respect to the raw material, 2-tert-butylphenol, is preferably 1 equivalent or more, and more preferably 1 to 3 equivalents or so.

The reaction time is preferably 10 minutes to 24 hours.

The reaction temperature is preferably −20° C. or lower, and more preferably −25° C. or lower.

In Step (i), it is desirable that the solution be highly diluted. Specifically, the amount of solvent used with respect to 2-tert-butylphenol is preferably 10 to 50 times by weight.

Performing the reaction under conditions of such low temperature and high dilution avoids degradation of the raw materials, and enables high yields of 1-(3-tert-butyl-4-hydroxyphenyl)ethanone.

1-(3-tert-Butyl-4-hydroxyphenyl)ethanone can be obtained as crystals by adding water to the reaction solution after the reaction is completed.

In Step (ii) where 1-(3-tert-butyl-4-hydroxyphenyl)ethanone is halogenated, reacting the compound with a halogenating reagent in a solvent yields compound (XII).

The halogenating reagent differs depending on the halogen of interest, and examples include N-bromosuccinimide (NBS), bromine, and such for bromination, N-chlorosuccinimide (NCS), chlorine, and such for chlorination, and N-iodosuccinimide (NIS), iodine, combinations of N-chlorosuccinimide (NCS) and sodium iodide, and such for iodination.

The solvent can be any solvent that does not inhibit the reaction. For example, ethers such as THF, esters such as ethyl acetate, amides such as N,N-dimethylformamide, 1-methyl-2-pyrrolidinone, and N,N-dimethylimidazolidinone, may be preferably used.

These solvents may be used individually or in combinations of two or more types of solvents.

The amount of halogenating reagent used with respect to 1-(3-tert-butyl-4-hydroxyphenyl)ethanone is preferably 1 equivalent or more, and more preferably 1 to 3 equivalents or so.

The reaction temperature is preferably 10° C. or lower, and more preferably in the range between −25° C. and 5° C. The formation of impurities can be suppressed by performing the reaction within this range.

The reaction time is preferably 10 minutes to 24 hours or so.

Compound (XV)

The compound of the present invention is a compound represented by formula (XV)

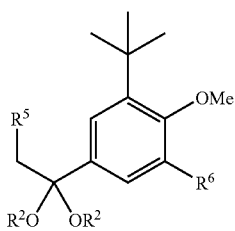

(XV)

(wherein, each of the two $R^2$s represents a $C_{1-4}$ alkyl group, and the two $R^2$s can be bonded to each other to form a cyclic group represented by —$(CH_2)_n$— (wherein, n represents an integer of 2 to 4); $R^5$ represents a hydrogen atom or a halogen atom, and $R^6$ represents a halogen atom or a morpholino group) or a salt thereof.

Specific examples of such compounds include the following compounds, and all of them are novel compounds.

(Compound IX)

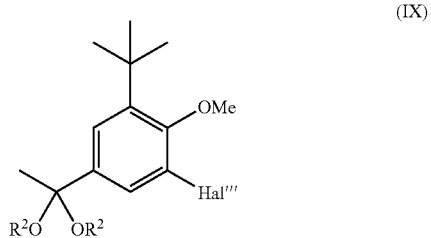

(IX)

In formula (IX), each of the two $R^2$s represents a $C_{1-4}$ alkyl group, and the two $R^2$s may be bonded to each other to form a cyclic group represented by —$(CH_2)_n$— (wherein, n represents an integer of 2 to 4).

Examples of the $C_{1-4}$ alkyl group include a methyl group, an ethyl group, an n-propyl group, an isopropyl group, an n-butyl group, a sec-butyl group, a tert-butyl group, and such. Among them, a methyl group is preferred. Furthermore, when two $R^2$s bond with each other to form a cyclic ketal, n is preferably 2 or 3, and more preferably 2.

Hal''' represents a halogen atom, and examples of the halogen atom include a chlorine atom, a bromine atom, and an iodine atom.

(Compound X)

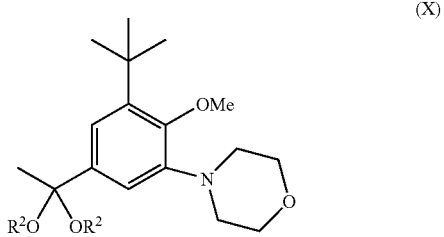

(X)

In formula (X), $R^2$ has the same meaning as $R^2$ in formula (IX).

(Compound XI)

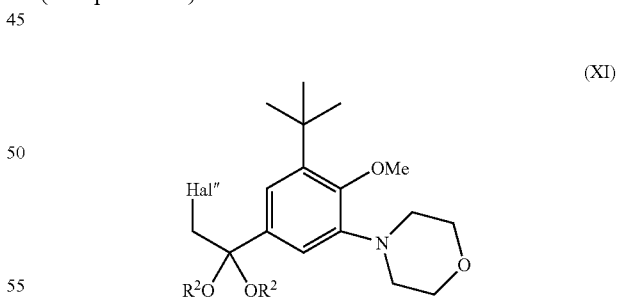

(XI)

In formula (XI), $R^2$ has the same meaning as $R^2$ in formula (IX). Hal" represents a halogen atom, and examples of such include a chlorine atom, a bromine atom, and an iodine atom. Among them, a bromine atom is preferred.

These compounds may serve as intermediates in generating the morpholine-substituted phenacyl derivative (B).

<Cyclic Benzamidine Derivative (C)>

In the present invention, the method for producing the cyclic benzamidine derivative (C) represented by formula (XIII) (may also be referred to as compound (XIII))

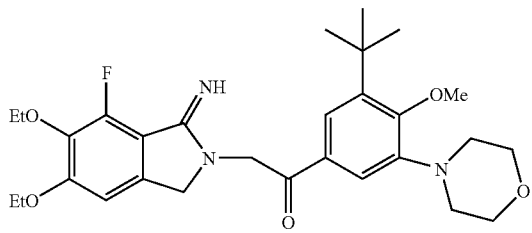

(XIII)

or a salt thereof is a method comprising the step of reacting the fluorinated cyclic benzamidine derivative (A) represented by formula (II)

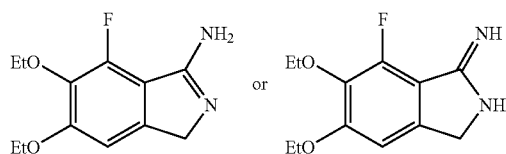

(II)

with the morpholine-substituted phenacyl derivative (B) represented by formula (VIII)

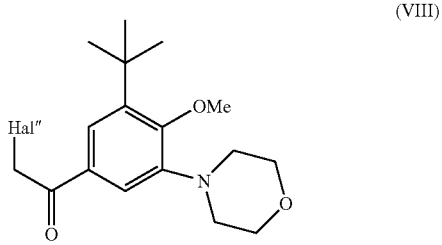

(VIII)

(wherein, Hal″ represents a halogen atom), using a hydrocarbon or ether as the solvent.

Generally, the reaction can be carried out by simply mixing these compounds (A) and (B) and stirring in a solvent. Furthermore, post-reaction treatments and procedures of isolation and purification may also be performed to isolate and purify the desired cyclic benzamidine derivative (C) as a free benzamidine or a salt thereof.

Examples of ethers that are used as the solvent include THF.

Examples of hydrocarbons that are used as the solvent include n-hexane, n-heptane, benzene, toluene, and xylene, and among them, aliphatic hydrocarbons such as n-hexane and n-heptane are preferred.

These solvents can be used individually or in combinations of two or more types of solvents.

When the ether or hydrocarbon is used as a solvent in the reaction, the salt of cyclic benzamidine derivative (C) is precipitated from the reaction system as crystals. Therefore, the extreme simplicity involved in isolating and purifying the cyclic benzamidine derivative (C) salt of interest is industrially advantageous.

Among these solvents, an ether is preferable and THF is particularly preferable. When using an ether such as THF as the solvent, the ether may be used alone or mixed with a non-ether poor solvent.

Examples of the poor solvent include hydrocarbons such as n-hexane, n-heptane, benzene, toluene, and xylene. Among them, n-heptane may be preferably used. Addition of such a poor solvent after completion of the reaction as an after-treatment increases the salt yield of the cyclic benzamidine derivative (C) (compound (XIII)).

When using ether as the solvent with an additionally mixed poor solvent, the ether proportion in the solvent is preferably 50 weight % or more and less than 100 weight %.

A poor solvent is added following the reaction with ether, and when the ether proportion in the solvent falls within the above range, precipitation of crystals can be performed with increased efficiency.

The reaction temperature is preferably 0° C. to room temperature or so, and the reaction time is preferably 10 minutes to 50 hours or so.

The fluorinated cyclic benzamidine derivative (A) and the morpholine-substituted phenacyl derivative (B), which are the raw materials for the cyclic benzamidine derivative (C), can be produced by known methods or by the production methods of the present invention. Preferably, they are produced by the above-mentioned methods of the present invention for producing the fluorinated cyclic benzamidine derivative (A) and/or by those used for producing the morpholine-substituted phenacyl derivative (B). It is desirable from the perspective of increasing overall yields to react the fluorinated cyclic benzamidine derivative (A) with the morpholine-substituted phenacyl derivative (B). The phrase "(A) and/or (B)" means at least either (A) or (B) is included.

The methods of the present invention for producing the cyclic benzamidine derivative (C) or a salt thereof may comprise a recrystallization step. More specifically, the cyclic benzamidine derivative (C) or a salt thereof obtained by the aforementioned methods can be further purified by recrystallization.

The recrystallization method involves adding crude crystals of the cyclic benzamidine derivative (C) or a salt thereof into a mixed solvent containing water and alcohol such as methanol or ethanol in a discretionary ratio, or a mixed solvent containing water and ether such as THF in a discretionary ratio, and dissolving the crude crystals at low temperatures. For example, after dissolution, additional water can be added to precipitate the crystals. A mixed solvent comprising alcohol and water is preferable. For the alcohol, ethanol is preferred.

For the dissolution above, the volume ratio of water to ether or water to alcohol in the mix is preferably 0:100 to 80:20, and more preferably in the range between 10:90 and 30:70.

The temperature at which crude crystals precipitate is preferably 50° C. or lower, and more preferably 45° C. or lower. The cyclic benzamidine derivative (C) and a salt thereof are unstable to heat, and when they are placed under high temperatures for a long period of time, their quality may decrease due to degradation, generation of by-products, and such. For example, when a mixed solvent comprising water and ethanol is used, the cyclic benzamidine derivative (C) or a salt thereof can be easily dissolved at low temperatures, and thus, their quality is not decreased by the heating needed for dissolution. Furthermore, since ethanol is used, this method is very safe from operational and pharmaceutical aspects. In addition, it is industrially advantageous since crystals are precipitated simply by adding water.

The cyclic benzamidine derivative (C) or a salt thereof obtained by such methods of the present invention have excellent thrombin receptor inhibitory activity, and are useful as thrombin receptor antagonists.

BEST MODE FOR CARRYING OUT THE INVENTION

Figure 1:
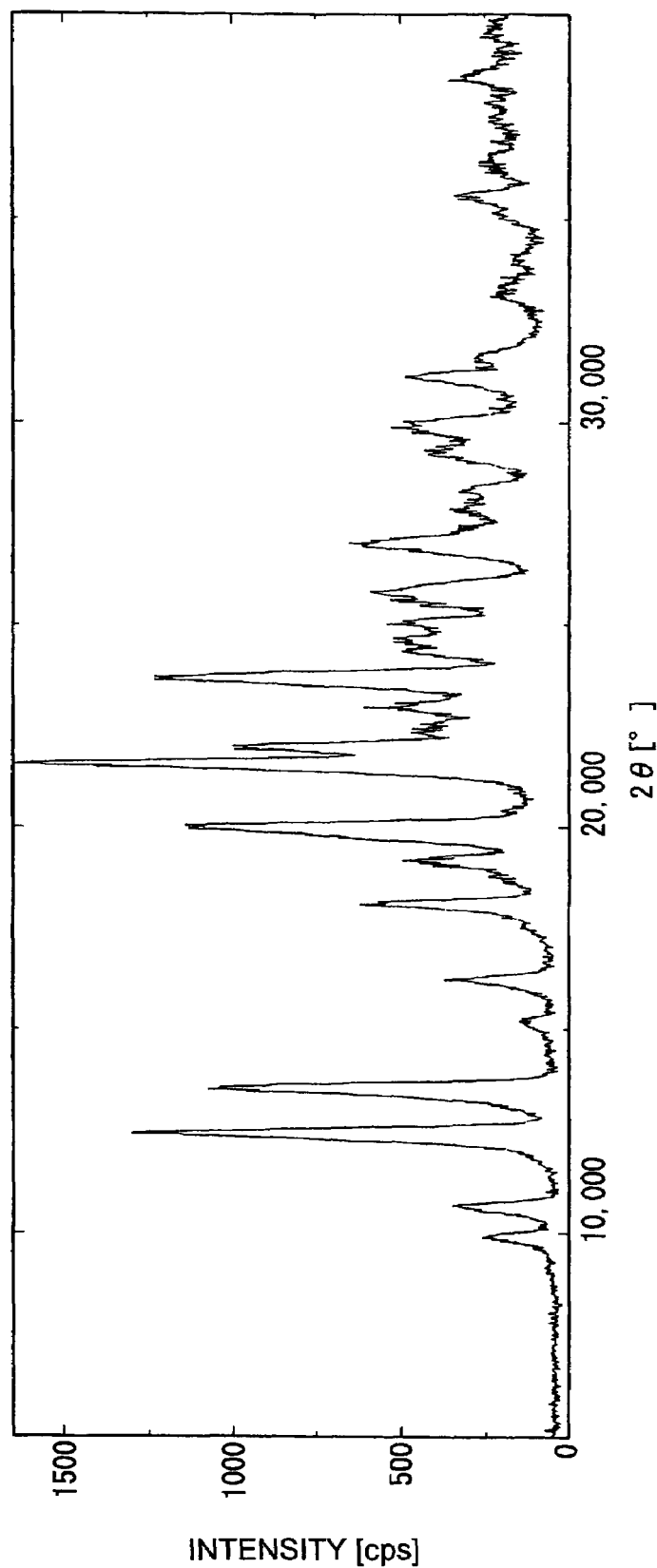
FIG. 1 is a powder X-ray diffraction pattern of crystals of compound (XIII).

The present invention will be explained in detail below with reference to Examples, but it is not to be construed as being limited thereto. In the present invention, room temperature refers to a temperature in the range of 20 to 30° C., and is preferably around 25° C.

PREPARATION EXAMPLE 1

1-Bromo-3,4-diethoxy-2-fluorobenzene

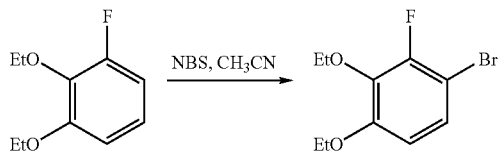

A solution of N-bromosuccinimide (NBS) (153.72 g, 864 mmol) in acetonitrile (1.5 L) was added dropwise to a solution of 1,2-diethoxy-3-fluorobenzene (150.00 g, 814 mmol) in acetonitrile (900 mL) on ice, and this was stirred at room temperature overnight. After the solvent was distilled off, ethyl acetate was added to the residue and washed with water. The obtained aqueous layer was extracted again with ethyl acetate, and the extract was combined with the aforementioned organic layer. The organic layer was washed sequentially with water, saturated brine, and water again, and was dried over anhydrous magnesium sulfate. The solution was concentrated and an oily substance was obtained. Following hexane addition to the oily substance, crystals that have precipitated were removed by filtration. The remaining solution was concentrated to yield an oily substance, which was distilled under reduced pressure to obtain 205.65 g of the subject compound (yield: 96%).

b.p ° C.: 110-111° C./2 mmHg $^1$H-NMR(CDCl$_3$)δ:1.35 (3H, t, J=6.8 Hz), 1.42 (3H, t, J=6.8 Hz), 4.03 (2H, q, J=6.8 Hz), 4.11 (2H, q, J=6.8 Hz), 6.57 (1H, dd, J=2.0, 9.3 Hz), 7.15 (1H, dd, J=7.3, 8.8 Hz).

MS m/z: 262(M$^+$)

EXAMPLE 1

3,4-Diethoxy-2-fluorobenzonitrile

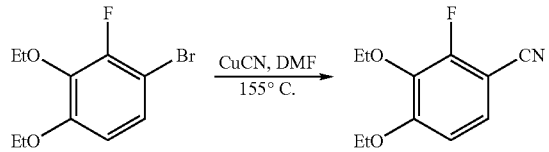

Copper(I)cyanide (6.8 g, 68.3 mmol) was added to a solution of 1-bromo-3,4-diethoxy-2-fluorobenzene (12.0 g, 45.6 mmol) in N,N-dimethylformamide (DMF) (60 mL) at room temperature, and this was then stirred at 155° C. for 3 hours. The reaction solution was cooled on ice. Following addition of ethyl acetate and 28% aqueous ammonia, the organic layer was separated and washed with water and saturated brine, and then dried over anhydrous magnesium sulfate. The solvent was removed after filtration, and the residue was purified by silica gel column chromatography (n-hexane, ethyl acetate) to give 9.0 g of the subject compound (yield: 94.3%).

$^1$H-NMR(CDCl$_3$)δ: 1.35 (3H, t, J=6.8 Hz), 1.49 (3H, t, J=6.8 Hz), 4.14 (2H, q, J=6.8 Hz), 4.15 (2H, q, J=6.8 Hz), 6.70 (1H, dd, J=1.5, 8.8 Hz), 7.24 (1H, dd, J=6.4, 8.8 Hz).

MS m/z: 209 (M$^+$)

EXAMPLE 2

3,4-Diethoxy-2-fluoro-6-formylbenzonitrile

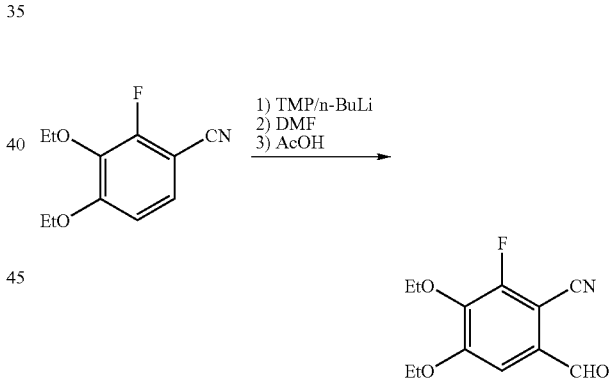

THF (18.7 kg) was transferred to a reaction vessel under a nitrogen gas stream. n-heptane (13.7 kg) and then 2,2,6,6-tetramethylpiperidine (TMP) (7.50 kg, 53.1 mol) were added, followed by stirring. The system was sealed, placed under a slightly positive nitrogen pressure, cooled to −15° C., and stirred overnight. The internal temperature was brought to −42.3° C., and 15% n-butyl lithium-hexane solution (22.4 kg, 50.2 mol) was added dropwise at an internal temperature of −10° C. or lower. The dropping tube was rinsed with n-heptane (0.68 kg). The internal temperature was then cooled to −86.9° C., and a solution of 3,4-diethoxy-2-fluorobenzonitrile (7.00 kg, 33.5 mol) in THF (10.68 kg) was added dropwise. The dropping tube was rinsed with THF (1.8 kg). Approximately 1 hour later, a solution of N,N-dimethylformamide (4.89 kg, 66.9 mol) in THF (4.49 kg) was added dropwise. 33 minutes after the dropwise addition of DMF-THF solution was completed, n-heptane (34.5 kg) was added dropwise. After stirring for 1 hour, a solution of acetic acid (10.5 kg, 175.0 mol) in THF (2.99 kg) was added dropwise, and the outer bath temperature was set to 10° C. 55 minutes later, water (50.4 L) was added dropwise, and then n-heptane (17.2 kg) was added. The outer bath temperature was set to 10° C., and the mixture was stirred for 14.7 hours. The reaction solution was extracted, and centrifuged half at a time. The obtained crystals were washed with n-heptane (5L), water (5L), and then n-heptane (5 L), to get 4.85 kg of crude material, and this was stored in a refrigerator. The other slurry was treated in the same manner as the first, and 5.25 kg of crude material was obtained (total amount of wet material: 10.10 kg).

The wet material was transferred to a reaction vessel, and water (40 L) and n-heptane (80 L) were added, followed by stirring at 25° C. for 18.7 hours. The reaction solution was removed, and the vessel walls were rinsed with a solution mixture comprising n-heptane (5 L) and water (10 L). The reaction solution was combined with the rinse solution and centrifuged. The obtained crystals were washed with n-heptane (5 L), water (5 L), and then n-heptane (5 L), to give 10.30 kg of the subject compound as a wet material.

The wet material was placed in a conical dryer, dried at 50° C. for 20 hours and then at 55° C. for 4 hours under reduced pressure to give 5.93 kg of the subject compound as slightly greenish white powdery crystals (yield: 75.3%).

$^1$H-NMR(CDCl$_3$)δ:1.39 (3H, t, J=6.8 Hz), 1.49 (3H, t, J=6.8 Hz), 4.20 (2H, q, J=6.8 Hz), 4.28 (2H, q, J=6.8 Hz), 7.32 (1H, d, J=1.5 Hz), 10.19 (1H, s)

MS m/z: 238 [(M+H)$^+$]

EXAMPLE 3

3,4-Diethoxy-2-fluoro-6-hydroxymethylbenzonitrile

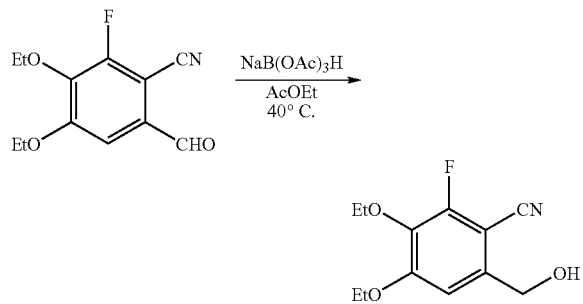

3,4-Diethoxy-2-fluoro-6-formylbenzonitrile (5.90 kg, 24.87 mol) and ethyl acetate (59.0 L) were transferred to a reaction vessel under a nitrogen atmosphere, and while stirring, sodium triacetoxyborohydride (NaB(OAc)$_3$H) (11.70 kg) was added. After 30 minutes of stirring, the internal temperature was heated up to 40° C., and the reaction solution was stirred for another 2 hours. The reaction solution was cooled, and at 15° C. internal temperature, water (2 L) was slowly added in drops, and excess sodium triacetoxyborohydride was degraded. Then more water (27.5 L) was added. The insoluble material was dissolved by increasing the outer bath temperature to 40° C., and the solution was separated after cooling. Following separation, the obtained organic layer was washed twice with an aqueous sodium bicarbonate solution and then with brine. The obtained organic layer was cooled in a 10° C. outer bath, and left to stand overnight.

The outer bath temperature was adjusted to 50° C., and the solution was concentrated under reduced pressure to approximately 14 L of liquid. The outer bath temperature was adjusted to 10° C., and n-heptane (59 L) was added, followed by 2.8 hours of stirring. Precipitated crystals were collected by filtration and washed with n-heptane (5.9 L) to obtain 5.66 kg of the subject compound as a wet material. This wet material was dried under reduced pressure at 50° C. for 18.3 hours in a conical dryer, and 5.17 kg of the subject compound was obtained as slightly yellowish white powdery crystals (yield: 87%).

$^1$H-NMR(CDCl$_3$)δ:1.36 (3H, t, J=6.8 Hz), 1.48 (3H, t, J=6.8 Hz), 4.12 (2H, q, J=6.8 Hz), 4.17 (2H, q, J=6.8 Hz), 4.82 (2H, s), 5.53 (1H, s), 6.95 (1H, s).

MS m/z: 240 (M+H)$^+$

EXAMPLE 4

3,4-Diethoxy-2-fluoro-6-methylbenzonitrile

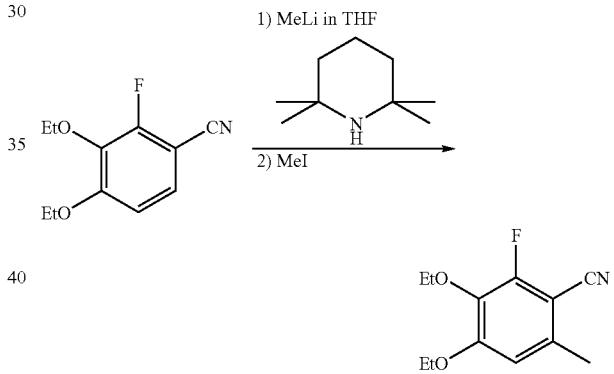

Under a stream of nitrogen gas, methyl lithium (1.03 M diethyl ether solution, 18.2 mL, 18.8 mmol) was added to an ice-cooled solution of 2,2,6,6-tetramethylpiperidine (3.16 mL, 18.7 mmol) in tetrahydrofuran (30 mL), followed by 30 minutes of stirring. After cooling the reaction system to −78° C., a solution of 3,4-diethoxy-2-fluorobenzonitrile (3.90 g, 18.6 mmol) in tetrahydrofuran (20 mL) was added dropwise, and 30 minutes later, methyl iodide (1.4 mL, 22.4 mmol) was added dropwise, followed by 2 hours of stirring. The reaction system was gradually warmed to room temperature, and 1N hydrochloric acid was added to the reaction solution, after which ethyl acetate extraction was performed. The extract was washed with water and saturated brine, and then dried over anhydrous magnesium sulfate. After filtration, the solvent was distilled off, and the residue was purified by silica gel column chromatography (n-hexane, ethyl acetate) to give 3.40 g of the subject compound (yield: 81.7%).

$^1$H-NMR(CDCl$_3$)δ:1.37 (3H, t, J=7.2 Hz), 1.49 (3H, t, J=7.2 Hz), 2.48 (3H, s), 4.08~4.16 (4H, m), 6.57 (1H, s).

MS m/z: 224 (M+H)$^+$

EXAMPLE 5

6-(Bromomethyl)-3,4-diethoxy-2-fluorobenzonitrile

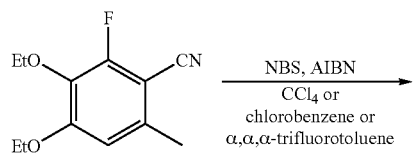

N-bromosuccinimide (553 mg, 3.05 mmol) and 2,2'-azobisisobutyronitrile (AIBN) (102 mg, 0.609 mmol) were added to a solution of 3,4-diethoxy-2-fluoro-6-methylbenzonitrile (679 mg, 3.04 mmol) in carbon tetrachloride (7 mL) at room temperature, and then this was refluxed for 5 hours. After cooling the reaction solution was washed with water and saturated brine, and then dried over anhydrous magnesium sulfate. After filtration, the solvent was distilled off, and the residue was purified by silica gel column chromatography (n-hexane, ethyl acetate) to give 614 mg of the subject compound (yield: 66.8%), and 121 mg of the raw material was recovered (yield: 17.8%).

$^1$H-NMR(CDCl$_3$)δ:1.38 (3H, t, J=7.2 Hz), 1.50 (3H, t, J=7.2 Hz), 4.16 (4H, q, J=7.2 Hz), 4.55 (2H, s), 6.81 (1H, s).

MS m/z: 302 (M+H)$^+$

EXAMPLE 6

6-(Bromomethyl)-3,4-diethoxy-2-fluorobenzonitrile

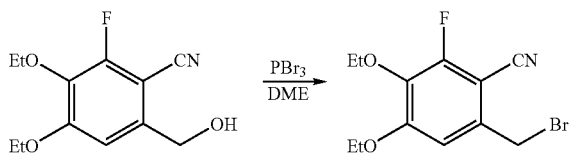

Phosphorus tribromide (PBr$_3$, 1.57 mL, 16.7 mmol) was added to a solution of 3,4-diethoxy-2-fluoro-6-(hydroxymethyl)benzonitrile (38.0 g, 33.4 mmol) in 1,2-dimethoxyethane (DME) (80 mL) on ice, followed by 3 hours of stirring at room temperature. After the reaction solution was cooled on ice, ethyl acetate and water were added. The organic layer was separated, and the aqueous layer was extracted further with ethyl acetate. The combined extract solutions were washed with saturated aqueous sodium hydrogen carbonate solution and saturated brine, and after addition of activated charcoal, were dried over anhydrous magnesium sulfate. After filtration, the solvent was distilled off, followed by addition of n-heptane (100 mL) to the residue, and the solvent was distilled off again. n-Heptane (100 mL) was added to the residue, and this was cooled on ice. Precipitated crystals were collected by filtration, and washed with n-heptane to give 9.1 g of the subject compound (yield: 90.1%).

$^1$H-NMR(CDCl$_3$)δ:1.38 (3H, t, J=7.2 Hz), 1.50 (3H, t, J=7.2 Hz), 4.16 (4H, q, J=7.2 Hz), 4.55 (2H, s), 6.81 (1H, s).

MS m/z: 302 (M+H)$^+$

EXAMPLES USING AMMONIA GAS (EXAMPLES 7, 8, AND 9)

EXAMPLE 7

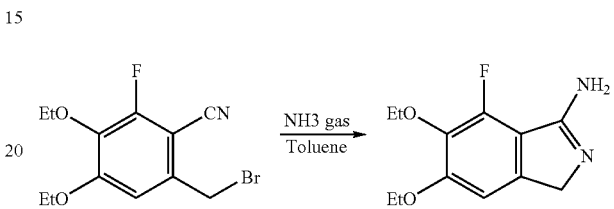

5,6-Diethoxy-7-fluoro-3H-isoindol-1-ylamine 6-(Bromomethyl)-3,4-diethoxy-2-fluorobenzonitrile (175.1 g, 579.5 mmol) was dissolved in toluene (2 L) and this was filtered under reduced pressure. This toluene solution was loaded into a reaction vessel together with toluene (16 L) and stirred at room temperature, and the air inside of the reaction vessel was replaced with ammonia gas. After replacing with ammonia gas in the reaction vessel at an internal pressure of 7.8 kg/cm$^2$, the system was sealed and stirred at room temperature for 15 hours. After releasing the ammonia gas, the air inside of the reaction vessel was replaced with nitrogen. Water (2.2 L) and 2 N hydrochloric acid (2.2 L) were added, and the solution was separated. After 1 N hydrochloric acid (1.3 L) was added to the organic layer, the solution was separated. The aqueous layer was combined with the aqueous layer obtained earlier and filtered through Celite, and then the filter was washed with water (1.3 L). 2 N aqueous sodium hydroxide (1.58 L) was added dropwise to the filtrate on ice while stirring, and the aqueous solution was adjusted to pH6.5. This was stirred at room temperature for approximately 5 hours. Then, 2 N aqueous sodium hydroxide solution (1.7 L) was added dropwise on ice while stirring to adjust the pH to 11.1, and crystals were precipitated. The crystals were collected by filtration, washed with water (1.75 L), and dried under reduced pressure overnight (40° C.) to give the subject compound as white crystals (110.3 g, yield: 80%, HPLC purity: 99.3%).

EXAMPLE 8

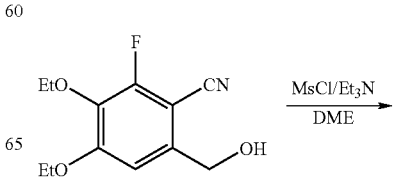

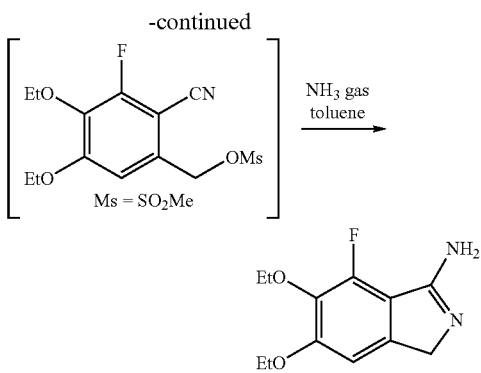

2-Cyano-4,5-diethoxy-3-fluorobenzyl methanesulfonate 3,4-Diethoxy-2-fluoro-6-(hydroxymethyl)benzonitrile (4.50 kg, 18.81 mol) and 1,2-dimethoxyethane (45 L) were loaded into a reaction vessel, followed by stirring. The reaction solution was cooled, and the system was placed under nitrogen atmosphere. At an internal temperature of 8.4° C., triethylamine (2.47 kg, 24.45 mol) was added. Furthermore, methanesulfonyl chloride (2.59 kg, 22.61 mol) was added dropwise without warming the internal temperature over 20° C. After stirring for 34 minutes, the system was placed under a stream of nitrogen gas, and the cooling was stopped. Toluene (45 L) and 0.5 N hydrochloric acid (9 L) were added, and the solution was separated. The obtained organic layer was washed with water (18 L), 10% aqueous sodium hydrogen carbonate solution (18 L), 10% brine (18 L), and water (18 L), and the organic layer was concentrated under reduced pressure. After adding toluene (45 L) to the concentrated solution, this was concentrated again under reduced pressure. The concentrated solution was cooled and diluted with toluene (40 L), and the diluted solution from the reaction vessel was equally divided into two containers. The walls of the reaction vessel were rinsed with toluene (5 L). This rinsing solution was divided in half and mixed with the aforementioned diluted solutions to give toluene solutions of 2-cyano-4,5-diethoxy-3-fluorobenzyl methanesulfonate. They were named solution A and solution B, and after measuring the weight of the solutions (solution A; 32.16 kg, solution B: 32.24 kg), the solutions were sampled and quantified by HPLC.

Solution of 2-cyano-4,5-diethoxy-3-fluorobenzyl methanesulfonate toluene

Properties: brown toluene solution; quantitative value: 5.79 kg (solution A: 2.92 kg, solution B: 2.87 kg); yield: 96.9%; HPLC purity: solution A 98.8%, solution B 98.6%

$^1$H-NMR (400 MHz, CDCl$_3$)δ:1.38 (3H, t, J=6.8 Hz), 1.50 (3H, t, J=6.8 Hz), 3.13 (3H, s), 4.17 (4H, q, J=6.8 Hz), 5.28 (2H, s), 6.89 (1H, d, J=1.0 Hz).

MS m/z: 317 (M$^+$)

EXAMPLE 9

5,6-Diethoxy-7-fluoro-3H-isoindol-1-ylamine

Solution A: 2-cyano-4,5-diethoxy-3-fluorobenzyl methanesulfonate in toluene [32.16 kg (2.92 kg 2-cyano-4,5-diethoxy-3-fluorobenzyl methanesulfonate), 9.20 mol], obtained in Example 8 was transferred to a reaction vessel with toluene (170 L), followed by stirring under room temperature. The reaction solution was cooled to 20° C. or less, and after stirring was stopped, the air inside of the system was replaced with ammonia. After stirring, ammonia was added again and the pressure was raised to 0.86 MPa. Without further treatment, the reaction solution was stirred overnight, and then ammonia gas was released. After adding water (35 L) to the reaction solution, 2 N hydrochloric acid (35 L) was added, and the solution was separated. 1 N hydrochloric acid (23.4 L) was added to the obtained organic layer, and the solution was separated. The obtained aqueous layer was mixed with the earlier aqueous layer, and this was clarified by filtration and transferred to a reaction vessel after rinsing with water (10 L). The reaction solution was rinsed with water (15 L) and cooled. 5 N aqueous sodium hydroxide solution (7.18 L) was added dropwise to the reaction solution, which was then kept warm in a 30° C. outer bath and stirred for approximately 4 hours. The reaction solution was cooled, then at the reaction solution temperature of 17.4° C., 5 N aqueous sodium hydroxide solution (12.82 L) was added dropwise, followed by overnight stirring. Precipitated crystals were filtered, and washed with water (30 L) and tert-butyl methyl ether (6 L) to obtain 2.29 kg of wet material. This wet material was dried under reduced pressure at 40° C. in a conical dryer, and the subject compound (1.85 kg) was obtained as slightly yellowish white powdered crystals.

Properties: slightly yellowish white powdered crystals; yield: 1.85 kg; percent yield: 84%; HPLC purity: 97.5%; water content: 0.22%.

$^1$H-NMR (400 MHz, DMSO-d$_6$)δ:1.24 (3H, t, J=7.0 Hz), 1.34 (3H, t, J=7.0 Hz),4.01 (2H, q, J=7.0 Hz), 4.17 (2H, q, J=7.0 Hz), 4.38 (2H, s), 6.04 (2H, bs), 7.04 (1H, s).

MS m/z: 239 (M+H)$^+$

EXAMPLES USING LIQUID AMMONIA (EXAMPLES 10 AND 11)

EXAMPLE 10

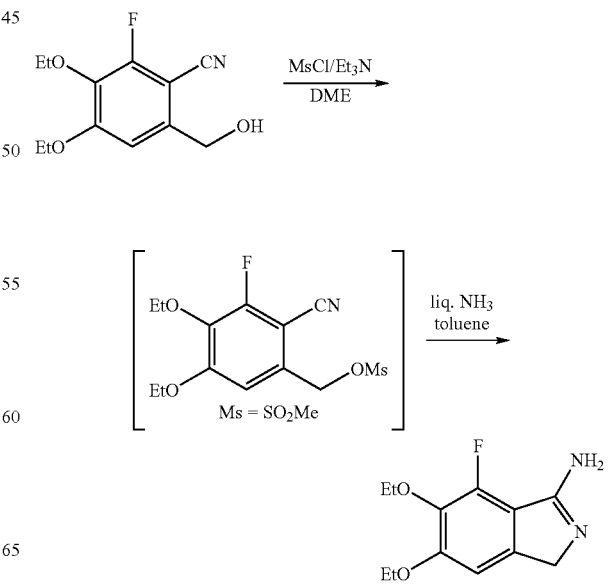

2-Cyano-4,5-diethoxy-3-fluorobenzyl methanesulfonate 3,4-Diethoxy-2-fluoro-6-(hydroxymethyl)benzonitrile (1 g, 4.18 mmol) was dissolved in 1,2-dimethoxyethane (10 mL), and cooled in a constant temperature bath at 8° C. after addition of methanesulfonyl chloride (0.39 mL, 5.02 mmol). Triethylamine (0.76 mL, 5.43 mmol) was added dropwise to this solution at approximately 20° C. or less. After stirring at the same temperature for 1 hour, toluene (5 mL) and 0.5 N hydrochloric acid (2 mL) were added, and this was transferred to a separatory funnel and toluene (5 mL) was used for rinsing. After separation of the solution, sequential washing was carried out with water (4 mL), 10% aqueous sodium hydrogen carbonate solution (4 mL), 10% brine (4 mL), and water (4mL). After the organic layer was evaporated, toluene (4 mL) was added, and water was removed by azeotropic distillation. Toluene (4 mL) was added to the residue and this was used in the next step. HPLC analytical values for the toluene solution: 99.10% (toluene peak is disregarded).

$^1$H-NMR (400 MHz, CDCl$_3$)δ:1.38 (3H, t, J=6.8 Hz), 1.50 (3H, t, J=6.8 Hz), 3.13 (3H, s), 4.17 (4H, q, J=6.8 Hz), 5.28 (2H, s), 6.89 (1H, s).

MS m/z: 317 (M$^+$.)

EXAMPLE 11

5,6-Diethoxy-7-fluoro-3H-isoindol-1-ylamine

A toluene solution of 2-cyano-4,5-diethoxy-3-fluorobenzyl methansulfonate obtained in Example 10 was transferred to a 100-mL autoclave, and toluene (9 mL) was used for rinsing. The autoclave was connected to a liquid ammonia cylinder, and this was cooled in an ethanol/dry ice bath. 9.1 g of ammonia was accumulated in the autoclave and this was placed in a constant temperature bath set at 8° C. After stirring for 1 hour (0.4 MPa), the ammonia was released. The reaction material was transferred to a separatory funnel and 26 mL of 1 N hydrochloric acid was used.

The aqueous layer was transferred to a flask, followed by addition of water (10.8 mL×8), and cooled on ice. 5 N aqueous sodium hydroxide solution (1.5 mL) was added to adjust the pH to 6.5. This was heated in a 30° C. water bath, stirred for approximately 3 hours, and again cooled on ice. 5 N aqueous sodium hydroxide (4.6 mL) was added to adjust the pH to 11.9. Crystals were collected by filtration, washed sequentially with water (13 mL,×10) and tert-butylmethyl ether (2.6 mL), and dried under reduced pressure. 0.851 g of the subject compound in yellowish white color was obtained (cumulative yield from two steps: 85.4%).

$^1$H-NMR (400 MHz, DMSO-d$_6$)δ:1.24 (3H, t, J=7.0 Hz), 1.34 (3H, t, J=7.0 Hz), 4.01 (2H, q, J=7.0 Hz), 4.17 (2H, q, J=7.0 Hz), 4.38 (2H, s), 6.04 (2H, bs), 7.04 (1H, s).

MS m/z: 239 (M+H)$^+$

EXAMPLE 12

3,4-Diethoxy-2-fluoro-6-(phthalimide methyl)benzonitrile

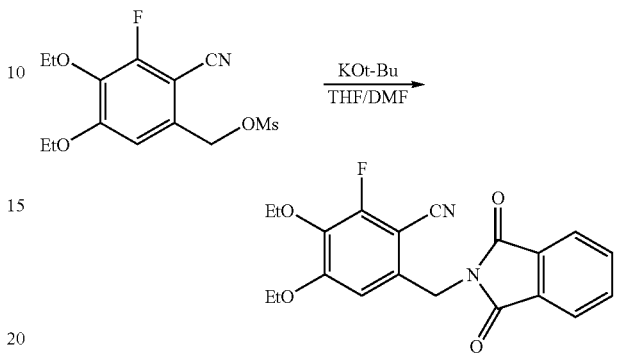

Phthalimide (510 mg, 3.47 mmol) was dissolved in THF (20 mL), and to this, potassium tert-butoxide (460 mg, 4.10 mmol) and a solution of 2-cyano-4,5-diethoxy-3-fluorobenzyl methanesulfonate (1 g, 3.15 mmol) in N,N-dimethylformamide (10 mL) were sequentially added. The weighing container was rinsed with N,N-dimethylformamide (10 mL). The solution was heated at 50° C. for 1 hour and cooled on ice. After adding ethyl acetate (120 mL) and water (80 mL), the solution was separated, and then the organic layer was washed twice with water (40 mL, 20 mL). The organic layer was evaporated under reduced pressure, and 1.165 g of the subject compound was obtained as crude crystals. Purification of these crystals by column chromatography yielded 972 mg of the subject compound (yield: 83.8%).

$^1$H-NMR (DMSO-d$_6$)δ:1.23 (3H, t, J=7.1 Hz), 1.30 (3H, t, J=7.1 Hz), 4.05 (2H, q, J=7.1 Hz), 4.11 (2H, q, J=7.1 Hz), 4.85 (2H, s), 6.96 (1H, s), 7.82-7.93 (4H, m).

MS m/z: 369 (M+H)$^+$

EXAMPLE 13

5,6-Diethoxy-7-fluoro-3H-isoindol-1-ylamine

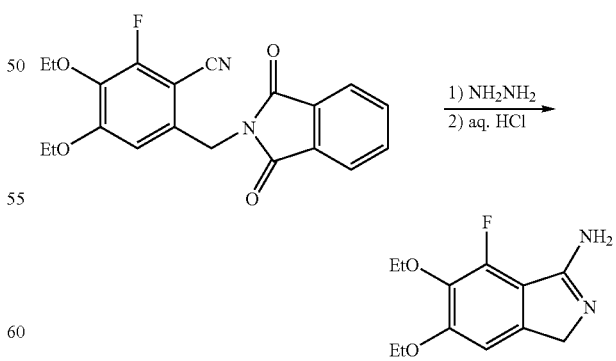

Tetrahydrofuran (3.5 mL) was added to 3,4-diethoxy-2-fluoro-6-(phthalimide methyl)benzonitrile (350 mg, 0.95 mmol), and this was degassed twice by reducing the pressure. Hydrazine hydrate (0.12 mL, 2.47 mmol) was added at room temperature, followed by stirring at the same temperature for 2.5 hours. After cooling on ice, 1 N hydrochloric acid (3.5 mL) was added. The solution was then brought back to room temperature, and stirred for approximately 3 hours. Only the tetrahydrofuran was distilled off, and precipitated crystals were filtrated. The filtrate was cooled on ice, and 5 N aqueous sodium hydroxide (0.6 mL) was added to adjust the pH to 6.2. Stirring was continued at room temperature. Approximately 2 hours later, water (10 mL) was added, and the presence of the substance of interest was confirmed by HPLC. The sample was cooled on ice, and then 5 N aqueous sodium hydroxide (0.5 ML) was added to adjust the pH to 12.4. The precipitated crystals were collected by filtration, washed with water (1 mL×5), and dried under reduced pressure at room temperature to obtain 169 mg of the subject compound (yield: 74.7%).

$^1$H-NMR (DMSO-d$_6$)δ:1.24 (3H, t, J=7.0 Hz), 1.34 (3H, t, J=7.0 Hz), 4.01 (2H, q, J=7.0 Hz), 4.17 (2H, q, J=7.0 Hz), 4.38 (2H, s), 6.04 (2H, bs), 7.04 (1H, s).

MS m/z: 239 (M+H)$^+$

PREPARATION EXAMPLE 2

1-(3-tert-Butyl-4-hydroxyphenyl)ethanone

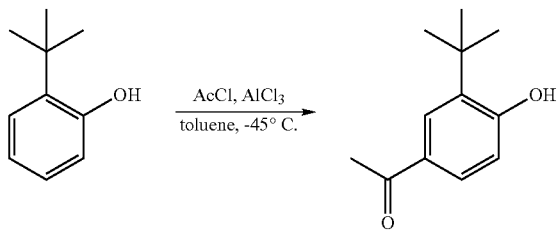

Aluminum chloride (44.4 g, 333 mmol) was cooled to −45° C., and toluene (1.25 L) was added followed by 2-tert-Butylphenol (50.0 g, 333 mmol). The sample was then stirred for 2 hours. In addition, acetyl chloride (26.1 g, 333 mmol) was added dropwise, followed by 2.5 hours of stirring. The reaction solution was added dropwise to ice-cold water (250 mL), and then this was stirred at room temperature. Crystals were collected by filtration and dried under reduced pressure (50° C.) to give 48.7 g of the subject compound as white crystals (yield: 76.1%, HPLC purity: 99.8%).

$^1$H-NMR (400 MHz, CDCl$_3$)δ:1.43 (9H, s), 2.57 (3H, s), 6.17 (1H, s), 6.76 (1H, d, J=8.0 Hz), 7.73 (1H, dd, J=2.4, 8.0 Hz), 7.96 (1H, d, J=2.4 Hz).

MS m/z: 193 [(M+H)$^+$]

PREPARATION EXAMPLE 3

1-(5-Bromo-3-tert-butyl-4-hydroxyphenyl)ethanone

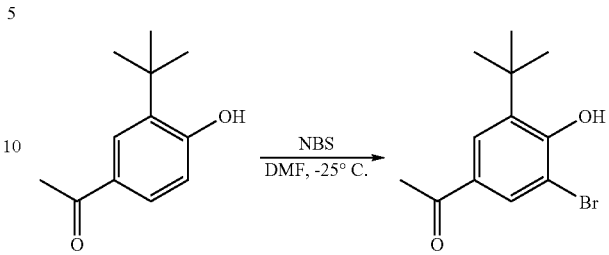

1-(3-tert-Butyl-4-hydroxyphenyl)ethanone (690.9 g, 3.75 mol) was dissolved in acetonitrile (6.05 L), and a solution of N-bromosuccinimide (701.28 g, 3.94 mol) in acetonitrile (5 L) was added dropwise while stirring on ice. After heating to room temperature, the solvent was concentrated to approximately 3 L. For extraction, n-heptane (5 L) and water (5 L) were added, and the solution was separated. The aqueous layer was extracted further with n-heptane (2 L), and the solution was separated. The organic layers were combined, washed with 5% aqueous sodium thiosulfate (1 L) and water (2 L), and concentrated under reduced pressure (35° C.) to obtain 977.0 g of the subject compound as a brownish oily substance (yield: 99.1%, HPLC purity: 95.8%).

$^1$H-NMR (400 MHz, CDCl$_3$)δ:1.42 (9H, s), 2.55 (3H, s), 6.26 (1H, s), 7.88 (1H, d, J=2.0 Hz), 7.99 (1H, d, J=2.0 Hz).

MS m/z: 271 [(M+H)$^+$]

EXAMPLE 14

2-Bromo-6-tert-butyl-4-(1,1-dimethoxyethyl)anisole

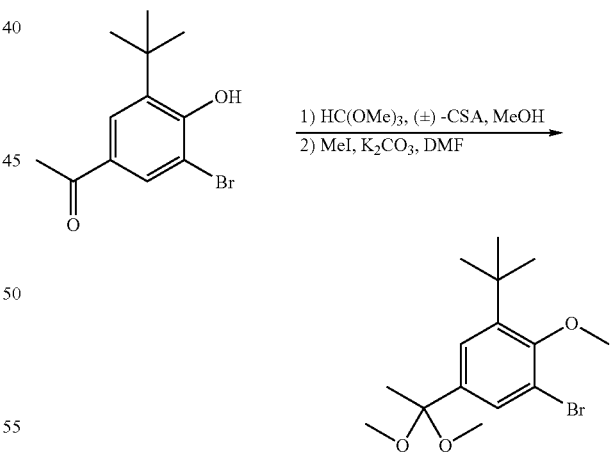

Under nitrogen atmosphere, methanol (678 mL), trimethyl orthoformate (796 g, 7.50 mol), and (±)-10-camphorsulfonic acid [(±)-CSA] (11.6 g, 0.050 mol, 2 mol %) were added to 1-(5-bromo-3-tert-butyl-4-hydroxyphenyl)ethanone (678 g, 2.50 mol), followed by stirring. After stirring for 2.7 hours, N,N-dimethylformamide (1.7 L) was added and this was cooled on ice. Furthermore, methyl iodide (700 g) was added followed by potassium carbonate (518 g), and this was stirred at room temperature. After stirring for 5.5 hours, water (4750 mL) and n-heptane (4750 mL) were added and the solution was separated. The organic layer was washed with water (2370 mL), and then sodium sulfate (120.2 g) was added. After stirring, the mixture was filtered by suction, and rinsed with n-heptane (250 mL). The filtrate was evaporated (50° C.) to obtain 808 g of the subject compound as a brown oily substance (yield: 98%, HPLC purity: 96.8%).

$^1$H-NMR (400 MHz, DMSO-$d_6$)δ:1.35 (9H, s), 1.43 (3H, s), 3.07 (6H, s), 3.86 (3H, s), 7.32 (1H, d, J=2.0 Hz), 7.47 (1H, d, J=2.0 Hz).

MS m/z: 330 (M$^+$)

EXAMPLE 15

1-(3-tert-Butyl-5-chloro-4-methoxyphenyl)ethanone

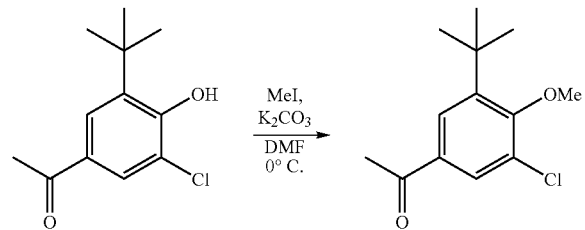

1-(3-tert-Butyl-5-chloro-4-hydroxyphenyl)ethanone (1.65 g, 7.28 mmol) and methyl iodide (2.07 g, 14.56 mmol) were added to N,N-dimethylformamide (2.5 mL), followed by stirring on ice, and addition of potassium carbonate (1.51 g, 10.92 mmol). After 3 hours of stirring, toluene (30 mL) and water (20 mL) were added, and the solution was separated. The organic layer was washed with water (15 mL), dried, and then concentrated under reduced pressure (50° C.) to obtain 1.37 g of the subject compound as a yellowish oily substance (yield: 78.2%, HPLC purity: 99.4%)

$^1$H-NMR (400 MHz, DMSO-$d_6$)δ:1.38 (9H, s), 2.57 (3H, s), 3.93 (3H, s), 7.81 (1H, d, J=2.0 Hz), 7.95 (1H, d, J=2.0 Hz).

EXAMPLE 16

6-tert-Butyl-2-chloro-4-(1,1-dimethoxyethyl)anisole

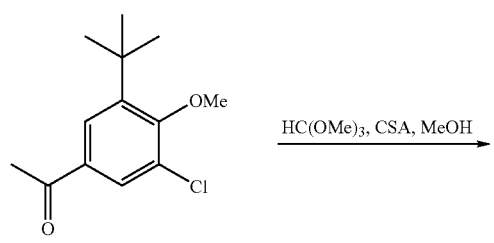

-continued

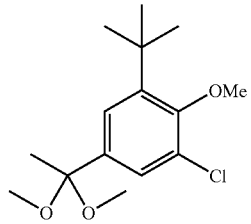

Methanol (1.4 mL), and trimethyl orthoformate (1.79 g, 16.95 mmol) were added to 1-(3-tert-butyl-5-chloro-4-methoxyphenyl)ethanone (1.36 g, 5.65 mmol), followed by stirring at room temperature. In addition, (±)-10-camphorsulfonic acid [(±)-CSA] (65 mg, 0.282 mmol, 5 mol %) was added, followed by 2 hours of stirring. Potassium carbonate (156 mg, 1.128 mmol) was added. After 40 minutes of stirring, water (10 mL) and n-heptane (10 mL) were added, and the solution was separated. After washing the organic layer with water (10 mL), the solvent was evaporated (50° C.) to obtain 1.57 g of the subject compound as a yellow oily substance (yield: 96.9%).

$^1$H-NMR (400 MHz, DMSO-$d_6$)δ:1.33 (9H, s), 1.44 (3H, s), 3.06 (6H, s), 3.87 (3H, s), 7.28 (1H, d, J=2.0 Hz), 7.31 (1H, d, J=2.0 Hz).

PREPARATION EXAMPLE 4

1-(3-tert-Butyl-4-hydroxy-5-iodophenyl)ethanone

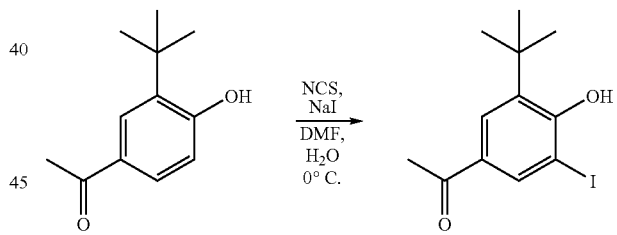

1-(3-tert-Butyl-4-hydroxyphenyl)ethanone (384 mg, 2 mmol) and sodium iodide (360 mg, 2.4 mmol) were dissolved in a mixed solution of N,N-dimethylformamide (3 mL) and water (1 mL), and this was cooled in an ice bath. While stirring, N-chlorosuccinimide (NCS) (320 mg, 2.4 mmol) was added portionwise over 10 minutes. After stirring for 50 minutes, 2% aqueous sodium thiosulfate (4 mL), 2 N hydrochloric acid (1 mL), and ethyl acetate (10 mL) were added, and the solution was separated. The organic layer was washed with a mixed solution of 2% aqueous sodium thiosulfate (5 mL) and saturated brine (1 mL), and then with saturated brine (5 mL). The organic layer was dried, and concentrated under reduced pressure (50° C.) to obtain 616 mg of the subject compound as a yellowish oily substance (yield: 96.8%, HPLC purity: 93.2%).

$^1$H-NMR (400 MHz, CDCl$_3$)δ:1.40 (9H, s), 2.54 (3H, s), 5.96 (1H, s), 7.90 (1H, d, J=2.0 Hz), 8.16 (1H, d, J=2.0 Hz).

EXAMPLE 17

1-(3-tert-Butyl-5-iodo-4-methoxyphenyl)ethanone

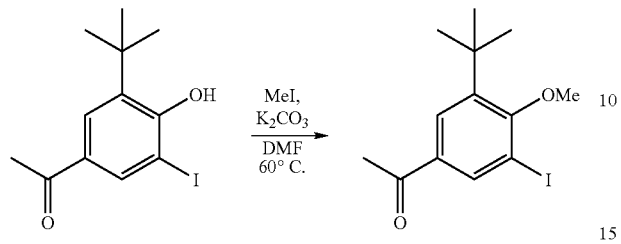

1-(3-tert-Butyl-4-hydroxy-5-iodophenyl)ethanone (616 mg, 1.93 mmol) was added to N,N-dimethylformamide (2.5 mL), and then methyl iodide (684 mg, 4.84 mmol) and potassium carbonate (401 mg, 2.90 mmol) were added, followed by 3 hours of stirring at 60° C. After cooling the mixture to room temperature, ethyl acetate (6 mL), water (3 mL), and 2 N hydrochloric acid (2 mL) were added, and the solution was separated. The organic layer was washed with a mixed solution of water (3 mL) and saturated brine (1 mL), followed by saturated brine (3 mL). The organic layer was dried and concentrated under reduced pressure (50° C.) to obtain 587 mg of the subject compound as a yellow oily substance (yield: 91.3%, HPLC purity: 94.1%).

$^1$H-NMR (400 MHz, CDCl$_3$)δ:1.41 (9H, s), 2.56 (3H, s), 3.94 (3H, s), 7.95 (1H, d, J=2.0 Hz), 8.26 (1H, d, J=2.0 Hz).

EXAMPLE 18

6-tert-Butyl-4-(1,1-dimethoxyethyl)-2-iodoanisole

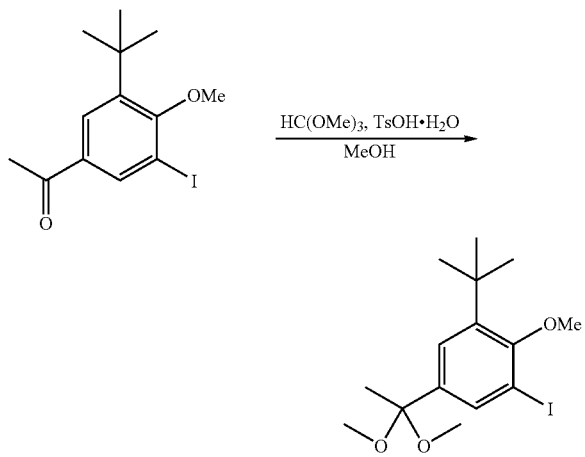

Methanol (6 mL), trimethyl orthoformate (262 mg, 2.4 mmol), and p-toluenesulfonic acid monohydrate (TsOH·H$_2$O) (38 mg, 0.2 mmol) were added to 1-(3-tert-butyl-5-iodo-4-methoxyphenyl)ethanone (664 mg, 2 mmol), and this was stirred at room temperature for 2 hours, and then at 60° C. for 1 hour. After stirring for another 3 hours at 0° C., potassium carbonate (138 mg, 1.0 mmol) was added, and after stirring for 1.5 hours on ice, the reaction solution was concentrated to dryness. Water (5 mL) and toluene (10 mL) were added to this residue and the solution was separated. The organic layer was washed with water (5 mL) and the solvent was distilled off (50° C.) to obtain 708 mg of the subject compound as pale brown crystals (yield: 93.6%).

$^1$H-NMR (400 MHz, DMSO-d$_6$)δ:1.34 (9H, s), 1.42 (3H, s), 3.06 (6H, s), 3.81 (3H, s), 7.34 (1H, d, J=2.0 Hz), 7.71 (1H, d, J=2.0 Hz).

EXAMPLE 19

4-[3-tert-Butyl-5-(1,1-dimethoxyethyl)-2-methoxyphenyl]morpholine

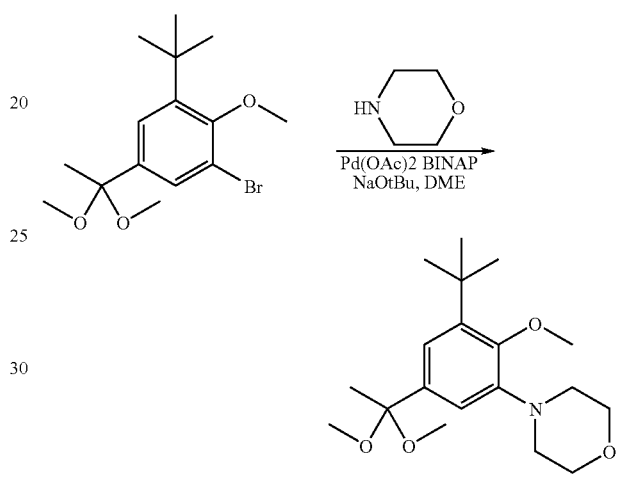

Under nitrogen atmosphere, 2-bromo-6-tert-butyl-4-(1,1-dimethoxyethyl)anisole (650 g, 1.962 mol), palladium acetate (4.4 g, 19.6 mmol, 1 mol %), and (±)-BINAP (18.3 g, 29.4 mmol, 1.5 mol %) were dissolved in 1,2-dimethoxyethane (1.96 L) at room temperature, and then morpholine (205 g, 2.36 mol) and sodium tert-butoxide (264 g, 2.75 mol) were added.

Following 2 hours of stirring at 85° C., the temperature was reduced to 30° C. or lower by stirring on ice. Insoluble materials were removed by filtration and the filter was washed with 1,2-dimethoxyethane (1 L). After distilling off the solvent under reduced pressure, methanol (600 mL), N,N-dimethylformamide (1.2 L), and n-heptane (6 L) were added, followed by extraction, and the solution was separated. The N,N-dimethylformamide layer was extracted twice with n-heptane (3 L), followed by separation of the solution, and then the n-heptane layers were combined, and washed with methanol (200 mL) and water (1.8 L). Thiocyanuric acid (TMT) (13 g) was added to the obtained n-heptane layer, followed by 15 hours of stirring at room temperature and then filtration through Celite. The filter was washed with n-heptane (500 mL). The filtrate was washed with 87% aqueous N,N-dimethylformamide (1.3 L) and water (1.3 L), and concentrated under reduced pressure (50° C.) to obtain 618 g of the subject compound as a brown oil (yield 93.3%, HPLC purity: 99.5%).

$^1$H-NMR (400 MHz, CDCl$_3$)δ:1.37 (9H, s), 1.52 (3H, s), 3.07 (4H, t, J=4.4 Hz), 3.18 (6H, s), 3.88 (4H, t, J=4.4 Hz), 3.94 (3H, s), 6.97 (1H, d, J=2.4 Hz), 7.10 (1H, d, J=2.4 Hz).

MS m/z: 337 (M$^+$).

EXAMPLE 20

2-Bromo-1-(3-tert-butyl-4-methoxy-5-morpholinophenyl)ethanone

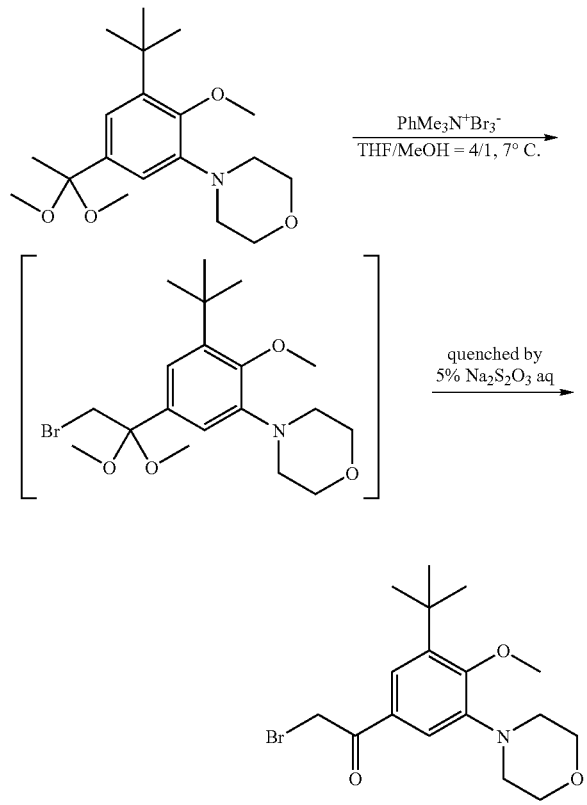

4-[5-(1,1-Dimethoxyethyl)-3-tert-butyl-2-methoxyphenyl]morpholine (600 g, 1.78 mol) was dissolved in a mixed solvent containing tetrahydrofuran (2.67 L) and methanol (0.89 L), and phenyltrimethylammonium tribromide (716 g, 1.87 mol) was added at 7° C. under a nitrogen atmosphere. After stirring for 1 hour, 5% aqueous sodium thiosulfate solution (660 mL) was added to the reaction solution. Then, water (4.68 L) was added, followed by 1 hour of stirring, and crystals were collected by filtration to give crude crystals of the subject compound as yellow skin-colored crystals.

The crude crystals of the subject compound were suspended and stirred in a mixed solvent containing n-heptane (1980 mL) and 2-propanol (660 mL) at 7° C. After stirring for 13 hours, crystals were collected by filtration, washed with 10% 2-propanol/n-heptane solution (660 mL) and n-heptane (660 mL), and then dried under reduced pressure (50° C.) to obtain 566.2 g of the subject compound as yellowish-white crystals (yield: 86.0%, HPLC purity: 99.0%).

4-[5-(2-Bromo-1,1-dimethoxyethyl)-3-tert-butyl-2-methoxyphenyl]morpholine $^1$H-NMR (400 MHz, CDCl$_3$)δ:1.37 (9H, s), 3.07 (4H, t, J=4.4 Hz), 3.24 (6H, s), 3.57 (2H, s), 3.88 (4H, t, J=4.4 Hz), 3.94 (3H, s), 6.98 (1H, d, J=2.4 Hz), 7.08 (1H, d, J=2.4 Hz).

2-Bromo-1-(3-tert-butyl-4-methoxy-5-morpholinophenyl)ethanone $^1$H-NMR (400 MHz, CDCl$_3$)δ:1.40 (9H, s), 3.09 (4H, t, J=4.4 Hz), 3.90 (4H, t, J=4.4 Hz), 3.99 (3H, s), 4.41 (2H, s), 7.52 (1H, d, J=2.0 Hz), 7.69 (1H, d, J=2.0 Hz).

MS m/z: 369 (M$^+$)

EXAMPLE 21

1-(3-tert-Butyl-4-methoxy-5-morpholinophenyl)-2-(5,6-diethoxy-7-fluoro-1-imino-1,3-dihydro-2H-isoindol-2-yl)ethanone hydrobromide

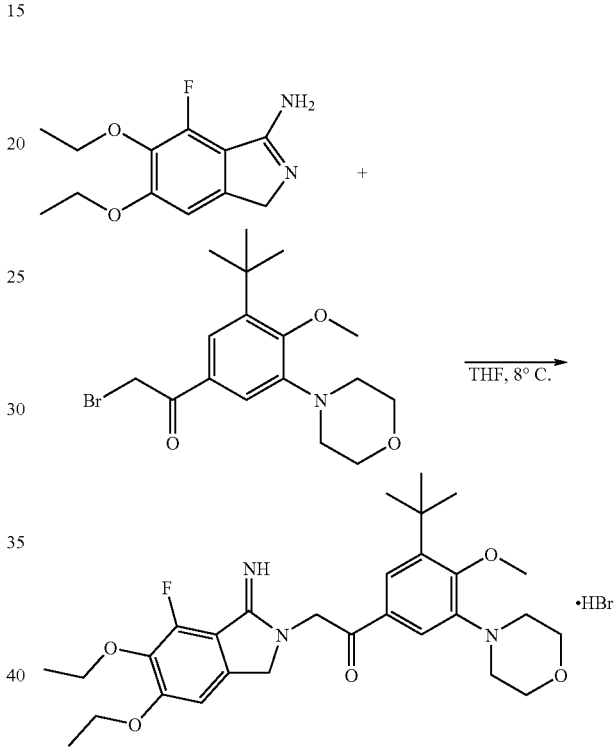

2-Bromo-1-(3-tert-butyl-4-methoxy-5-morpholinophenyl)ethanone (550 g, 1.485 mol) was dissolved in tetrahydrofuran (3 L) and clarified by filtration. While stirring at an external temperature of 6° C., a solution of 5,6-diethoxy-7-fluoro-3H-isoindole-1-ylamine (300 g, 1.254 mol) in tetrahydrofuran (4.5 L) was added dropwise in 3 portions (100 g/1.5 L×3). Following the dropwise addition, crystals were precipitated. After 18 hours of stirring, the precipitated crystals were collected by filtration, and washed with ice-cooled tetrahydrofuran (1.2 L) to obtain 696.5 g of the subject compound as wet crystals.

The wet crystals (693.5 g) were dissolved at 50° C. in 50% tetrahydrofuran/water (5 L), clarified by filtration, and rinsed with 50% tetrahydrofuran/water (0.5 L). While stirring on ice, water (2.5 L) was added to the filtrate, followed by seed crystals (1.52 g), and then water (7.5 L) was added dropwise. After stirring at 8° C. for 15 hours, the crystals were collected by filtration, washed with water (2 L), and then dried with a stream of air (60° C.) for 26 hours to obtain 622.1 g of the subject compound as white crystals (yield: 81.5%, HPLC purity: 99.6%).

Recrystallization Methods 1-(3-tert-Butyl-4-methoxy-5-morpholinophenyl)-2-(5,6-diethoxy-7-fluoro-1-imino-1,3-dihydro-2H-isoindol-2-yl)ethanone hydrobromide Ethanol (46.8 L) and water (8.3 L) were added to the crude crystal (5.50 kg) of the subject compound, and the crystal was dissolved by heating at 40° C. This solution was clarified by filtration, and ethanol (5.5 L) and water (5.5 L) were used for rinsing. Water (27.5 L) was added dropwise to the solution, and the internal temperature was cooled to 10.9° C. To this, seed crystals were added, followed by dropwise addition of water (82.5 L), and overnight stirring at the same temperature. The crystal was collected by filtration, and dried under reduced pressure to give 4.90 kg of the subject compound (yield: 89.1%).

Table 1 shows the X-ray diffraction data (2θ) (error range ±0.2) of the crystal obtained above when powder X-ray diffraction utilizing Cu Kα radiation as the characteristic X-ray was used. FIG. 1 shows the powder X-ray diffraction spectrum for the crystal. X-ray diffraction was carried out under the following conditions.

goniometer: horizontal goniometer
attachment: rotating sample holder (Reflection Method)
divergence slit: "1 deg"
scattering slit: "1 deg"
light receiving slit: "0.15 mm"
scanning mode: continuous
scanning speed: 2°/min
scanning step size: 0.02°
scanning range: 5 to 40°

TABLE 1

| Peak No. | X-ray diffraction data 2θ(°) | Intensity |
|---|---|---|
| 1 | 9.900 | 260 |
| 2 | 9.980 | 208 |
| 3 | 10.540 | 270 |
| 4 | 10.680 | 348 |
| 5 | 12.160 | 342 |
| 6 | 12.440 | 1288 |
| 7 | 13.560 | 1038 |
| 8 | 16.180 | 267 |
| 9 | 16.240 | 372 |
| 10 | 16.340 | 248 |
| 11 | 18.080 | 623 |
| 12 | 18.160 | 568 |
| 13 | 19.040 | 335 |
| 14 | 19.280 | 388 |
| 15 | 19.720 | 685 |
| 16 | 19.960 | 1130 |
| 17 | 20.040 | 1140 |
| 18 | 21.560 | 1643 |
| 19 | 21.940 | 918 |
| 20 | 22.000 | 997 |
| 21 | 22.320 | 455 |
| 22 | 23.060 | 517 |
| 23 | 23.520 | 855 |
| 24 | 23.680 | 1195 |
| 25 | 23.780 | 1045 |
| 26 | 24.200 | 367 |
| 27 | 24.320 | 452 |
| 28 | 24.580 | 520 |
| 29 | 24.660 | 522 |
| 30 | 25.100 | 493 |

TABLE 1-continued

| Peak No. | X-ray diffraction data 2θ(°) | Intensity |
|---|---|---|
| 31 | 25.480 | 443 |
| 32 | 25.600 | 460 |
| 33 | 25.760 | 548 |
| 34 | 25.820 | 590 |
| 35 | 26.080 | 345 |
| 36 | 26.940 | 615 |
| 37 | 27.000 | 655 |
| 38 | 27.140 | 492 |
| 39 | 27.440 | 330 |
| 40 | 27.920 | 312 |
| 41 | 28.080 | 303 |
| 42 | 28.400 | 290 |
| 43 | 29.200 | 420 |
| 44 | 29.400 | 397 |
| 45 | 29.880 | 470 |
| 46 | 30.060 | 387 |
| 47 | 31.200 | 415 |
| 48 | 31.600 | 270 |

As described above, in the present invention, compound (II) can be synthesized in good yield by employing compounds (I), (III), (IV), (V), (VI), (VII), (XVI), and (XVIII) as the intermediates. More specifically, the conventional method described in WO02/85855 has an approximately 10% yield, whereas the method of the present invention has an approximately 40% yield. Therefore, the method of the present invention gives a remarkably increased yield when compared to conventional methods.

By employing the above-mentioned compounds (IX), (X), (XI), and (XII) as intermediates, compound (VIII) can be synthesized in good yield. More specifically, the conventional method described in WO02/85855 has only a few percent yield, whereas the yield by the method of this invention is approximately 50%. Therefore, the method of the present invention has a remarkably increased yield when compared to the conventional method.

In the above-mentioned coupling of compound (II) and compound (VIII), the reaction product is precipitated from the reaction mixture as a salt by employing a hydrocarbon or ether (preferably tetrahydrofuran) as the solvent, therefore, the target compound (XIII) can be isolated and purified very easily.

In the recrystallization of the cyclic benzamidine derivative (C) or a salt thereof, the cyclic benzamidine derivative (C) can be easily dissolved in a low temperature range where it can exist stably by employing a mixed solvent comprising an alcohol and water, or a mixed solvent comprising an ether and water (preferably a mixed solvent comprising an alcohol and water) as the solvent for dissolution. Furthermore, crystals can be easily precipitated by simply adding water to the solution.

INDUSTRIAL APPLICABILITY

The methods of the present invention for producing the fluorinated cyclic benzamidine derivative (A) or a salt thereof, enable convenient synthesis of the fluorinated cyclic benzamidine derivative (A) or a salt thereof with simple procedures and good yields, by using a novel compound (I), represented by formula (I) as the raw material for synthesis (wherein X represents a leaving group).

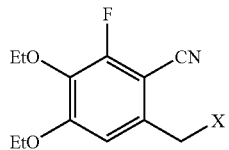

Furthermore, since the methods of this invention for producing the morpholine-substituted phenacyl derivative (B) or a salt thereof use a novel compound (8) represented by formula (IX) as the raw material for synthesis

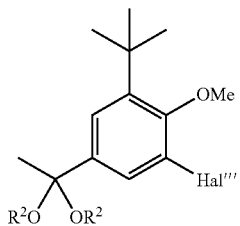

(wherein, each of the two $R^2$s represents an alkyl group of 1 to 4 carbons, and the two $R^2$s may be bonded to each other to form a cyclic group represented by —$(CH_2)_n$— (wherein, n represents an integer of 2 to 4); Hal''' represents a halogen atom), the morpholine-substituted phenacyl derivative (B) or a salt thereof can be easily synthesized by simple procedures.

Additionally, since the methods of the present invention for producing the cyclic benzamidine derivative (C) or a salt thereof, comprise the step of coupling the fluorinated cyclic benzamidine derivative (A) or a salt thereof with the morpholine-substituted phenacyl derivative (B) or a salt thereof, in the presence of at least one type of solvent selected from the group consisting of ethers and hydrocarbons, the desired cyclic benzamidine derivative (C) or a salt thereof can be easily crystallized and obtained with extreme ease.

In the methods of the present invention for recrystallizing the cyclic benzamidine derivative (C) or a salt thereof, the cyclic benzamidine derivative (C) is dissolved in a mixed solvent comprising an alcohol and water, or a mixed solvent comprising an ether and water, and then water is added to precipitate the crystals. Therefore, the cyclic benzamidine derivative (C) can be easily dissolved at low temperatures, and at the same time, recrystallized crystals can be easily obtained.

The invention claimed is:

1. A method for producing a fluorinated cyclic benzamidine derivative (A) represented by formula (II) (wherein Et represents an ethyl group), or a salt thereof,

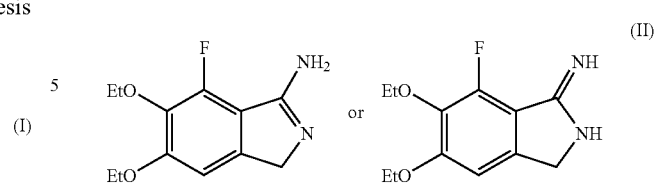

wherein the method comprises the step of reacting a compound represented by formula (I)

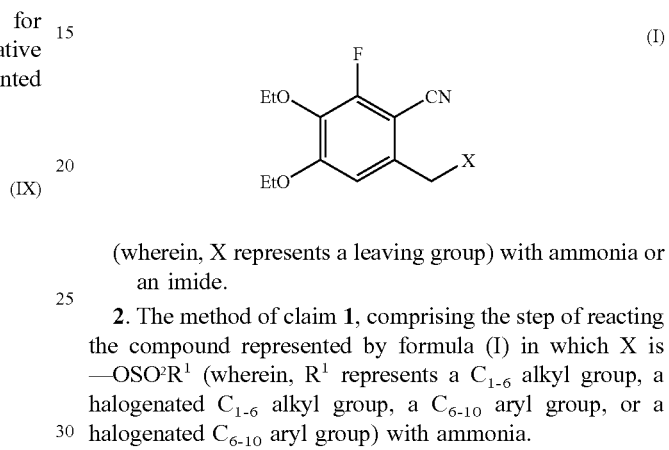

(wherein, X represents a leaving group) with ammonia or an imide.

2. The method of claim 1, comprising the step of reacting the compound represented by formula (I) in which X is —$OSO_2R^1$ (wherein, $R^1$ represents a $C_{1-6}$ alkyl group, a halogenated $C_{1-6}$ alkyl group, a $C_{6-10}$ aryl group, or a halogenated $C_{6-10}$ aryl group) with ammonia.

3. The method of claim 1, comprising the steps of:
(a) reacting the compound represented by formula (I) in which X is —$OSO_2R^1$ (wherein, $R^1$ represents a $C_{1-6}$ alkyl group, a halogenated $C_{1-6}$ alkyl group, a $C_{6-10}$ aryl group, or a halogenated $C_{6-10}$ aryl group), with a phthalimide or a succinimide, or a metal salt thereof, and
(b) converting the compound obtained in step (a) into an amine derivative.

4. The method of claim 1, comprising the step of reacting the compound represented by formula (I) in which X represents a halogen atom, with ammonia.

5. The method of claim 1, comprising the steps of:
(a) reacting the compound represented by formula (I) in which X represents a halogen atom, with a phthalimide or a succinimide, or a metal salt thereof, and
(b) converting the compound obtained in step (a) into an amine derivative.

6. The method of claim 2 or 3, wherein a compound represented by formula (I')

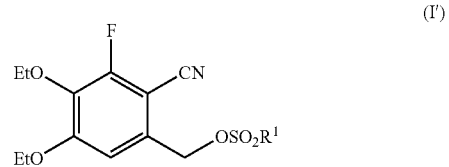

(wherein, $R^1$ represents a $C_{1-6}$ alkyl group, a halogenated $C_{1-6}$ alkyl group, a $C_{6-10}$ aryl group, or a halogenated $C_{6-10}$ aryl group) is obtained by reacting a compound represented by formula (III)

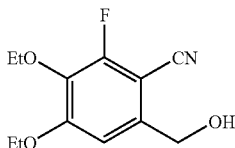

(III)

(wherein, Et represents an ethyl group), with R¹SO₂Y or (R¹SO₂)₂O (wherein, R¹ represents a $C_{1-6}$ alkyl group, a halogenated $C_{1-6}$ alkyl group, a $C_{6-10}$ aryl group, or a halogenated $C_{6-10}$ aryl group, and Y represents a halogen atom).

7. The method of claim 4 or 5, wherein the compound represented by formula (I″)

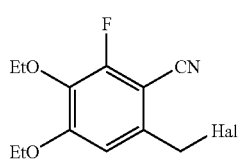

(I″)

(wherein, Hal represents a halogen atom) is obtained by reacting a compound represented by formula (III)

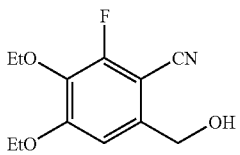

(III)

(wherein, Et represents an ethyl group) with a halogenating reagent.

8. The method of claim 4 or 5, wherein the compound represented by formula (I″)

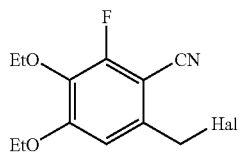

(I″)

(wherein, Hal represents a halogen atom), is obtained by reacting a compound represented by formula (IV)

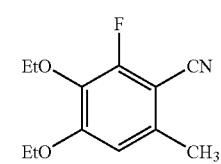

(IV)

(wherein, Et represents an ethyl group), with a halogenating reagent.

9. The method of claim 6, wherein the compound represented by formula (III) is obtained by steps comprising the following (1) to (3):

(1) reacting a compound represented by formula (V)

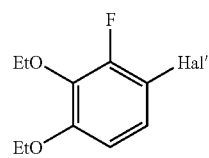

(V)

(wherein, Hal' represents a halogen atom) with a cyanation reagent to obtain a compound represented by formula (VI)

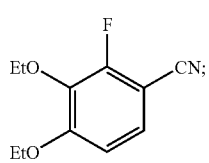

(VI)

(2) obtaining a compound represented by formula (VII)

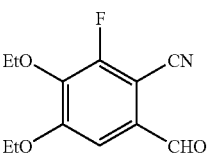

(VII)

through a formylation reaction of the compound represented by formula (VI); and (3) obtaining the compound represented by formula (III)

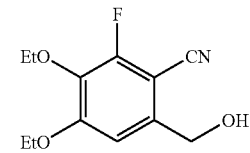

(III)

(wherein, Et represents an ethyl group) by reducing the compound represented by formula (VII).

10. The method of claim 4 or 5, wherein the compound represented by formula (I″)

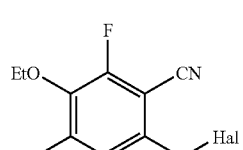

(I″)

(wherein, Hal represents a halogen atom) is obtained by steps (1') to (3') described below:

(1') reacting a compound represented by formula (V)

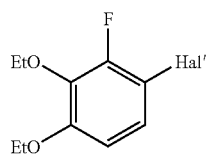

(V)

(wherein, Hal' represents a halogen atom) with a cyanation reagent to obtain a compound represented by formula (VI)

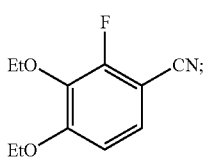

(VI)

(2') obtaining the compound represented by formula (IV)

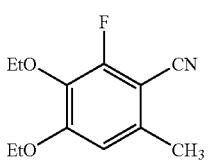

(IV)

through a methylation reaction of the compound represented by formula (VI); and (3') obtaining the compound represented by formula (I''') (wherein Et represents an ethyl group) by reacting the compound represented by formula (IV) with a halogenating reagent.

11. A method for producing a morpholine-substituted phenacyl derivative (B) represented by formula (VIII)

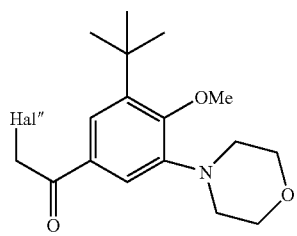

(VIII)

(wherein, Hal'' represents a halogen atom) or a salt thereof, wherein the method comprises the following steps of (1'') to (3''):

(1'') reacting a compound represented by formula (IX)

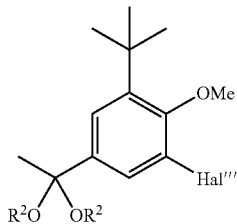

(IX)

(wherein, each of the two $R^2$s represents a $C_{1-4}$ alkyl group, and the two $R^2$s may be bonded to each other to form a cyclic group represented by —$(CH_2)_n$— (wherein, n represents an integer of 2 to 4); Hal''' represents a halogen atom) with morpholine to obtain a compound represented by formula (X)

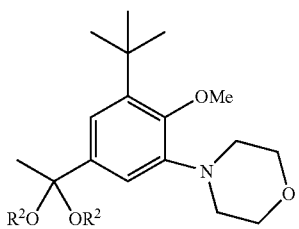

(X)

(wherein, $R^2$ represents the same group as in formula (IX));

(2'') reacting a compound represented by formula (X) with a halogenating reagent to obtain a compound represented by formula (XI)

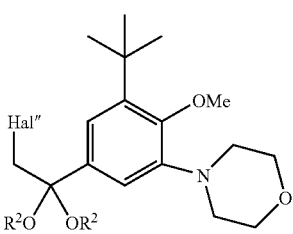

(XI)

(wherein, $R^2$ represents the same group as in formula (IX), and Hal'' represents a halogen atom);

(3'') performing a deketalization reaction on a compound represented by formula (XI) to obtain a morpholine-substituted phenacyl derivative (B) represented by formula (VIII) (In the above formulas, Me represents a methyl group).

12. The method of claim 11, wherein the compound represented by formula (IX)

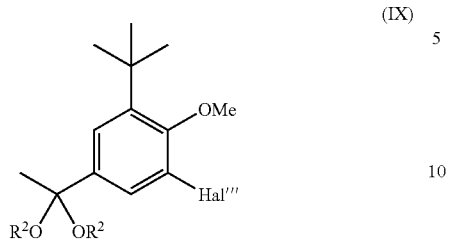

(IX)

(wherein, each of the two $R^2$s represents a $C_{1-4}$ alkyl group, and the two $R^2$s may be bonded to each other to form a cyclic group represented by —$(CH_2)_n$— (wherein, n represents an integer of 2 to 4, and Me represents a methyl group); Hal''' represents a halogen atom) is obtained through the steps of: ketalization of a compound represented by formula (XII)

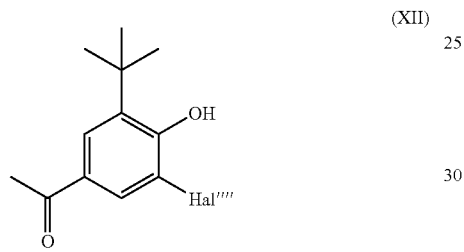

(XII)

(wherein, Hal'''' represents a halogen atom), by reacting with $R^2OH$, $HC(OR^2)_3$ (wherein $R^2$ represents a $C_{1-4}$ alkyl group), or HO—$(CH_2)_n$—OH (wherein, n represents an integer of 2 to 4); and methoxylation of the hydroxyl group in the compound represented by formula (XII).

13. A method for recrystallizing a cyclic benzamidine derivative (C), wherein the method comprises the steps of dissolving a compound represented by formula (XIII)

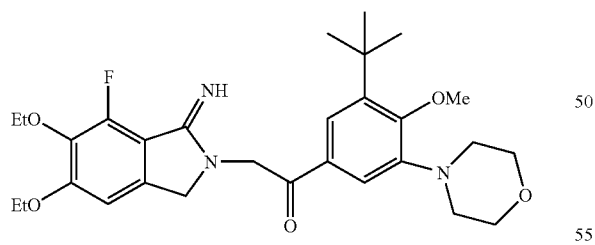

(XIII)

(wherein, Me represents a methyl group, and Et represents an ethyl group)), or the salt thereof, in a mixed solvent comprising an alcohol and water, or a mixed solvent comprising an ether and water; and after dissolution, adding additional water to precipitate crystals of the compound represented by formula (XIII)), or the salt thereof.

14. The recrystallization method of claim 13, wherein the mixed solvent is a mixed solvent comprising an alcohol and water.

15. A compound represented by formula (XIV)

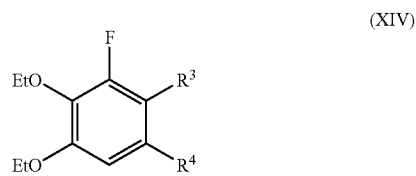

(XIV)

(wherein, $R^3$ represents a halogen atom or CN; $R^4$ represents a hydrogen atom, a methyl group, —CHO, —$CH_2OH$, —$CH_2Hal$ (wherein, Hal represents a halogen atom), —$CH_2$—$OSO_2R^1$ (wherein, $R^1$ represents a $C_{1-6}$ alkyl group, a halogenated $C_{1-6}$ alkyl group, a $C_{6-10}$ aryl group, or a halogenated $C_{6-10}$ aryl group), a phthalimide methyl group, or a succinimide methyl group; and Et represents an ethyl group).

16. A compound represented by formula (XV)

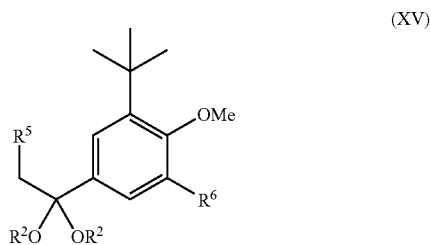

(XV)

(wherein, each of the two $R^2$s represents an alkyl group of 1-4 carbon atoms, and the two $R^2$s may be bonded to each other to form a cyclic group represented by —$(CH_2)_n$— (wherein, n represents an integer of 2 to 4); $R^5$ represents a hydrogen atom or a halogen atom, $R^6$ represents a halogen atom or a morpholino group, and Me represents a methyl group), or a salt thereof.

17. The method of claim 7, wherein the compound represented by formula (III) is obtained by steps comprising the following (1) to (3):

(1) reacting a compound represented by formula (V)

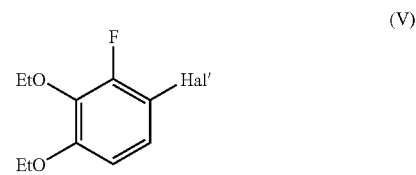

(V)

(wherein, Hal' represents a halogen atom) with a cyanation reagent to obtain a compound represented by formula (VI)

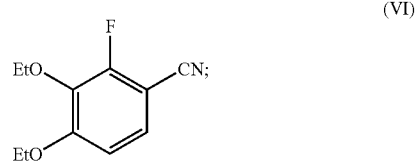

(VI)

(2) obtaining a compound represented by formula (VII)
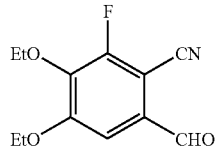
(VII)
through a formylation reaction of the compound represented by formula (VI); and
(3) obtaining the compound represented by formula (III)
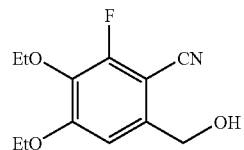
(III)
(wherein, Et represents an ethyl group) by reducing the compound represented by formula (VII).
* * * * *

UNITED STATES PATENT AND TRADEMARK OFFICE
CERTIFICATE OF CORRECTION

PATENT NO.        : 7,375,236 B2                                          Page 1 of 1
APPLICATION NO. : 11/208289
DATED             : May 20, 2008
INVENTOR(S)       : Shimomura et al.

It is certified that error appears in the above-identified patent and that said Letters Patent is hereby corrected as shown below:

In column 5, line 6, please delete "—$OSO^2R^1$" and insert -- —$OSO_2R^1$ --.

In column 12, line 41, please delete "—$CH^2$-$OSO_2R^1$" and insert -- —$CH_2$-$OSO_2R^1$ --.

In column 28, line 19, please delete "—$CH^2$-$OSO_2R^1$" and insert -- —$CH_2$-$OSO_2R^1$ --.

In column 60, claim 2, line 28, please delete "—$OSO^2R^1$" and insert -- —$OSO_2R^1$ --.

Signed and Sealed this

Third Day of February, 2009

JOHN DOLL
*Acting Director of the United States Patent and Trademark Office*